(12) United States Patent
Miyazawa et al.

(10) Patent No.: US 10,458,957 B2
(45) Date of Patent: Oct. 29, 2019

(54) ULTRASONIC DEVICE, ULTRASONIC MODULE, AND ULTRASONIC MEASURING DEVICE

(71) Applicant: Seiko Epson Corporation, Tokyo (JP)

(72) Inventors: Hiromu Miyazawa, Azumino (JP); Hiroshi Ito, Suwa (JP); Tomoaki Nakamura, Chino (JP); Masayoshi Yamada, Chino (JP); Kanechika Kiyose, Matsumoto (JP); Tsukasa Funasaka, Shiojiri (JP)

(73) Assignee: Seiko Epson Corporation (JP)

( * ) Notice: Subject to any disclaimer, the term of this patent is extended or adjusted under 35 U.S.C. 154(b) by 135 days.

(21) Appl. No.: 15/681,883

(22) Filed: Aug. 21, 2017

(65) Prior Publication Data
US 2018/0059067 A1 Mar. 1, 2018

(30) Foreign Application Priority Data
Aug. 24, 2016 (JP) .................................. 2016-163344

(51) Int. Cl.
*G01N 29/24* (2006.01)
*G01N 29/06* (2006.01)
(Continued)

(52) U.S. Cl.
CPC ........ *G01N 29/2437* (2013.01); *A61B 8/4411* (2013.01); *A61B 8/4483* (2013.01); *A61B 8/4494* (2013.01); *A61B 8/54* (2013.01); *B06B 1/0688* (2013.01); *G01N 29/0681* (2013.01); *G01N 29/221* (2013.01);
(Continued)

(58) Field of Classification Search
CPC .......... G01N 29/2437; G01N 29/0681; G01N 29/221; A61B 8/4411; A61B 8/4483; A61B 8/4494; A61B 8/54
See application file for complete search history.

(56) References Cited

U.S. PATENT DOCUMENTS

| | | | |
|---|---|---|---|
| 5,894,647 A | * | 4/1999 | Lakin ....................... H03H 3/04 29/25.35 |
| 6,515,402 B2 | | 2/2003 | Klee et al. |

(Continued)

FOREIGN PATENT DOCUMENTS

| | | |
|---|---|---|
| JP | 04-149078 A | 5/1992 |
| JP | 09-033498 A | 2/1997 |

(Continued)

*Primary Examiner* — Helen C Kwok
(74) *Attorney, Agent, or Firm* — Harness, Dickey & Pierce, P.L.C.

(57) ABSTRACT

An ultrasonic device includes: a substrate provided with a first opening and a second opening; a support film that is provided on the substrate and closes the first opening and the second opening; a transmitting piezoelectric film that is provided on the support film at a position which overlaps the first opening when viewed in a thickness direction of the substrate and that is sandwiched between a pair of electrodes in the thickness direction of the substrate; and a receiving piezoelectric film that is provided on the support film at a position which overlaps the second opening when viewed in the thickness direction of the substrate and that is sandwiched between a pair of electrodes in an intersecting direction intersecting with the thickness direction of the substrate.

7 Claims, 16 Drawing Sheets

(51) Int. Cl.
  *G01N 29/22* (2006.01)
  *A61B 8/00* (2006.01)
  *B06B 1/06* (2006.01)

(52) U.S. Cl.
  CPC .. *A61B 8/4427* (2013.01); *G01N 2291/02466* (2013.01); *G01N 2291/0426* (2013.01); *G01N 2291/102* (2013.01); *G01N 2291/105* (2013.01)

(56) References Cited

U.S. PATENT DOCUMENTS

| | | | |
|---|---|---|---|
| 6,972,510 B2 | 12/2005 | Klee et al. | |
| 7,019,604 B2* | 3/2006 | Gotoh | H03H 3/04 333/187 |
| 7,128,941 B2* | 10/2006 | Lee | H03H 3/04 427/58 |
| 7,868,522 B2* | 1/2011 | Ruby | H03H 3/04 310/312 |
| 8,692,441 B2* | 4/2014 | Dausch | B06B 1/0607 216/56 |
| 2002/0105250 A1 | 8/2002 | Klee et al. | |
| 2003/0141783 A1 | 7/2003 | Klee et al. | |
| 2011/0062535 A1* | 3/2011 | McMullen | B06B 1/0292 257/419 |
| 2011/0291207 A1* | 12/2011 | Martin | G10K 9/125 257/416 |
| 2011/0319766 A1* | 12/2011 | Tsuruno | A61B 8/04 600/454 |
| 2012/0025337 A1* | 2/2012 | Leclair | B81B 7/0048 257/419 |
| 2012/0206014 A1* | 8/2012 | Bibl | B06B 1/0644 310/331 |
| 2014/0066778 A1 | 3/2014 | Nishiwaki | |
| 2014/0103781 A1* | 4/2014 | Nakamura | H01L 41/09 310/334 |
| 2015/0105663 A1 | 4/2015 | Kiyose et al. | |
| 2015/0151330 A1* | 6/2015 | Tsuruno | B06B 1/0629 367/7 |
| 2015/0158052 A1* | 6/2015 | Latev | B06B 1/0622 310/316.01 |
| 2015/0273526 A1 | 10/2015 | Tsuruno et al. | |

FOREIGN PATENT DOCUMENTS

| | | |
|---|---|---|
| JP | 2002-271897 A | 9/2002 |
| JP | 2008-164464 A | 7/2008 |
| JP | 2010-154371 A | 7/2010 |
| JP | 2010147658 A | 7/2010 |
| JP | 2014-042714 A | 3/2014 |
| JP | 2014-195495 A | 10/2014 |
| JP | 2015-076825 A | 4/2015 |
| JP | 2015-195351 A | 11/2015 |

* cited by examiner

ULTRASONIC DEVICE, ULTRASONIC MODULE, AND ULTRASONIC MEASURING DEVICE

BACKGROUND

1. Technical Field

The present invention relates to an ultrasonic device, an ultrasonic module, and an ultrasonic measuring device.

2. Related Art

In the related art, an ultrasonic transducer using a so-called a bulk type piezoelectric body has been known as an ultrasonic transducer that performs a transmitting process and a receiving process of ultrasonic waves. The ultrasonic transducer includes a piezoelectric body sandwiched between a pair of electrodes and that applies a voltage between the electrodes so as to vibrate the piezoelectric body and transmits ultrasonic waves, or that detects an output voltage from the piezoelectric body to which ultrasonic waves are input and receives ultrasonic waves. However, such a bulk type piezoelectric body needs to have a large dimension in thickness, and thus it is difficult to obtain a thin or compact piezoelectric body.

In this respect, there has been known a thin-film type ultrasonic transducer using a thin piezoelectric film that is configured to include a vibration film provided to cover an opening of a support body having the opening and a piezoelectric film which is provided on the vibration film and is sandwiched between a pair of electrodes (for example, see JP-A-2002-271897).

Such an ultrasonic transducer vibrates the vibration film through the application of the voltage between the electrodes so as to transmit the ultrasonic waves and detects reception of the ultrasonic waves in response to the output voltage from the piezoelectric film by the vibration of the vibration film. With the ultrasonic transducer that vibrates the vibration film by using such a thin-film type piezoelectric body, it is possible to significantly reduce a thickness dimension thereof in an ultrasonic-wave transmitting/receiving direction, compared to the bulk type ultrasonic transducer, and thus it is possible to obtain a thin or compact ultrasonic measuring device.

Incidentally, the thin-film type ultrasonic transducer transmits the ultrasonic waves by the vibration of the vibration film and, then, detects reception of the ultrasonic waves through distortion of the piezoelectric film by the vibration film that vibrates in response to reflected ultrasonic waves. In this case, when the ultrasonic waves are transmitted, the vibration film is significantly displaced, and thereby high-output ultrasonic waves are output. When the ultrasonic waves are received, vibration is highly sensitively detected and the reception of the ultrasonic waves needs to be detected even in a case of small vibration of the vibration film. Hence, in order to achieve characteristics depending on respective functions, it is necessary to configure an ultrasonic transducer for transmission and a transducer for receiving.

In addition, in the ultrasonic transducer disclosed in JP-A-2002-271897, in order to have high receiving sensitivity during reception of the ultrasonic waves, it is preferable that a distance between the pair of electrodes increases. However, in the ultrasonic transducer disclosed in JP-A-2002-271897, the distance between the pair of electrodes is equal to a film thickness dimension of the piezoelectric film, and thus an increase in the distance between the pair of electrodes is limited thereto. In other words, when the distance greatly excesses the film thickness dimension of the piezoelectric film, the vibration film is inhibited from being displaced due to the stiffness of the piezoelectric film, and thus the receiving sensitivity decreases.

As described above, when the ultrasonic transducer disclosed in JP-A-2002-271897 is an ultrasonic transducer for both of transmission and reception or an ultrasonic transducer having the same configuration for transmission and for reception, a problem arises in that transmission/reception efficiency of the ultrasonic waves is reduced.

SUMMARY

An advantage of some aspects of the invention is to provide an ultrasonic device that has high transmission/reception efficiency of ultrasonic waves, an ultrasonic module, and an ultrasonic measuring device. Hereinafter, application examples and embodiments that can achieve the object will be described.

An ultrasonic device according to an application example includes: a substrate provided with a first opening and a second opening; a support film that is provided on the substrate and closes the first opening and the second opening; a transmitting piezoelectric film that is provided on the support film at a position which overlaps the first opening when viewed in a thickness direction of the substrate, and is sandwiched between a pair of electrodes in the thickness direction of the substrate; and a receiving piezoelectric film that is provided on the support film at a position which overlaps the second opening when viewed in the thickness direction of the substrate, and is sandwiched between a pair of electrodes in an intersecting direction intersecting with the thickness direction of the substrate. A film thickness dimension of the receiving piezoelectric film in the thickness direction of the substrate is smaller than a film thickness dimension of the transmitting piezoelectric film.

In this application example, the ultrasonic device includes an ultrasonic transducer for transmission (transmission transducer) and an ultrasonic transducer for reception (reception transducer). The transmission transducer has the support film (first vibration portion which is a region that overlaps the first opening in the support film) which covers the first opening of the substrate, the transmitting piezoelectric film, and the pair of electrodes (transmitting electrodes) by which the transmitting piezoelectric film is sandwiched in the film thickness direction. The reception transducer has the support film (second vibration portion which is a region that overlaps the second opening in the support film) which covers the second opening of the substrate, the receiving piezoelectric film, and the pair of electrodes (receiving electrodes) by which the receiving piezoelectric film is sandwiched in the intersecting direction intersecting with the film thickness direction. The receiving piezoelectric film is formed to have the film thickness thinner than that of the transmitting piezoelectric film.

In a case where the ultrasonic waves are transmitted by using the ultrasonic transducer that drives the piezoelectric film disposed on the vibration film so as to transmit and receive ultrasonic waves, and a predetermined drive voltage is applied between the electrodes, it is necessary to increase a displacement amount of the piezoelectric film. In this case, the displacement amount is qualitatively inversely proportional to the distance between the electrodes, and thus the distance between the electrodes is reduced. By comparison, in a case where the ultrasonic waves are received by the ultrasonic transducer, it is necessary to obtain a large signal (detection signal) from slight displacement of the vibration film. In this case, a signal value of detection signal is inversely proportional to the distance between the electrodes in a qualitative manner, and thus the distance between the electrodes is reduced.

In this application example, since the transmission transducer has a configuration in which the transmitting piezoelectric film is sandwiched between the pair of transmitting electrodes in the film thickness direction, the distance between the transmitting electrodes is equal to the film thickness dimension of the transmitting piezoelectric film. In this manner, it is possible to sufficiently increase the transmitting sensitivity (displacement amount (bending amount) of the vibration film obtained when a predetermined voltage is applied).

In addition, the reception transducer has a configuration in which the receiving piezoelectric film is sandwiched between the pair of receiving electrodes in the intersecting direction. In this case, it is possible to increase the distance between the pair of receiving electrodes, compared to a configuration in which the receiving piezoelectric film is sandwiched between the pair of receiving electrodes in the film thickness direction. Accordingly, it is possible to increase the receiving sensitivity.

In other words, in this application example, the transmission transducer and the reception transducer are provided as separate transducers, and thereby it is possible to have characteristics suitable for transmitting the ultrasonic waves in the transmission transducer and to have characteristics suitable for receiving the ultrasonic waves in the reception transducer. In addition, the electrodes, by which the receiving piezoelectric film is sandwiched, are disposed in the intersecting direction intersecting with the thickness direction of the receiving piezoelectric film, and thereby it is possible to remarkably increase the receiving sensitivity, compared to a case of a configuration in which the electrodes are disposed in the thickness direction of the receiving piezoelectric film and the receiving piezoelectric film is sandwiched.

In addition, the inventor of the invention finds that a product of a distortion amount (nm) of the first vibration portion obtained when a predetermined voltage is applied to the transmission transducer and receiving sensitivity (nV/Pa) in the reception transducer is defined as a figure of merit (nm·nV/Pa) of transmission and reception of the ultrasonic waves in the ultrasonic device, and the larger the figure of merit is, the higher the transmission/reception efficiency of the ultrasonic device is. In this application example, in the transmission transducer and the reception transducer having the configurations described above, the film thickness dimension of the receiving piezoelectric film is smaller than the film thickness dimension of the transmitting piezoelectric film. In this case, the figure of merit increases, compared to a case where the film thickness dimension of the transmitting piezoelectric film is smaller than the film thickness dimension of the receiving piezoelectric film. In other words, in the ultrasonic device including the transmission transducer and the reception transducer described above, the film thickness dimension of the receiving piezoelectric film is smaller than the film thickness dimension of the transmitting piezoelectric film, and thereby it is possible to improve the transmission/reception efficiency.

In the ultrasonic device according to the application example, it is preferable that the film thickness dimension of the transmitting piezoelectric film is 300 nm to 1800 nm, and the film thickness dimension of the receiving piezoelectric film is 80 nm or larger.

In this application example, while an occurrence of dielectric breakdown of the transmitting piezoelectric film and the receiving piezoelectric film is reduced, it is possible to obtain the ultrasonic device having high transmission/reception efficiency.

In other words, in the transmission transducer, one (lower transmitting electrode) of the pair of transmitting electrodes, the transmitting piezoelectric film (PZT), and the other (upper transmitting electrode) of the pair of transmitting electrodes are formed through film formation in this order on the vibration film made of $ZrO_2$ or the like. At this time, Pb atoms are dispersed to the lower transmitting electrode side during the film formation and burning of the transmitting piezoelectric film (PZT) in some cases. In general, the dispersion of the Pb atoms is stopped on an interface between the lower transmitting electrode and the vibration film ($ZrO_2$); however, the dispersion of the Pb atoms causes Pb defects to occur all over the transmitting piezoelectric film due to atoms and oxygen defects to occur. In this case, the oxygen defects are leak paths when a polarization voltage is applied in polarization treatment or the like, and thus hopping conduction of electrons increases. Finally, the dielectric breakdown occurs and the withstand voltage is reduced.

Here, when the film thickness dimension of the transmitting piezoelectric film is smaller than 300 nm, there is a high risk of occurrence of the dielectric breakdown, and thus reliability of the ultrasonic device is reduced. In addition, in a case where the film thickness dimension exceeds 1800 nm, it is difficult for the vibration film to be bent due to an influence of the stiffness of the transmitting piezoelectric film, and thus the transmitting sensitivity decreases. In this respect, in a case where the transmitting piezoelectric film has the film thickness in a range described above, it is possible to have a decrease in the risk of occurrence of the dielectric breakdown, and it is possible to reduce a decrease in the transmitting sensitivity.

By comparison, in the reception transducer, when the polarization treatment is performed, the polarization voltage is applied between the pair of receiving electrodes which is disposed in the intersecting direction. As described above, since the distance between the receiving electrodes is a sufficiently long distance, the withstand voltage is also sufficiently increased. Hence, even when the film thickness of the receiving piezoelectric film of the reception transducer is thinner than that of the transmitting piezoelectric film, there is a low risk of occurrence of the dielectric breakdown. However, when the film thickness of the receiving piezoelectric film is smaller than 80 nm, Pb atoms are dispersed in a film formation atmosphere during the film formation and the oxygen defects occur at the same time. Thus, there is a high risk of occurrence of the dielectric breakdown during the polarization treatment. In this respect, as in this application example, the film thickness of the receiving piezoelectric film is larger than 80 nm, and thereby it is possible to reduce the dielectric breakdown during the polarization treatment.

In the ultrasonic device according to the application example, it is preferable that the support film is provided with a first vibration portion that closes the first opening and a second vibration portion that closes the second opening. It is preferable that a transmission transducer is configured to have the first vibration portion and the transmitting piezoelectric film, and a reception transducer is configured to have the second vibration portion and the receiving piezoelectric film. It is preferable that a natural frequency of the transmission transducer is different from a natural frequency of the reception transducer.

In this application example, the transmission transducer and the reception transducer have different natural frequencies from each other. As described above, in this application example, the ultrasonic waves are transmitted from the transmission transducer, and the reception transducer receives ultrasonic waves reflected from a target subject; however, at this time, when the natural frequencies of the transmission transducer and the reception transducer are caused to be equal to each other and the ultrasonic waves are transmitted from the transmission transducer, the reception transducer resonates. In this case, the output voltage containing a noise component is output from the reception transducer, and has an influence on reception accuracy of the ultrasonic waves. In this respect, in this application example, the transmission transducer and the reception transducer have different natural frequencies from each other. In this manner, when the ultrasonic waves are transmitted, it is possible to reduce the resonance of the reception transducer, and it is possible to reduce an occurrence of a disadvantage of containing noise in the output voltage.

In the ultrasonic device according to the application example, it is preferable that a difference between the natural frequency of the transmission transducer and the natural frequency of the reception transducer is 0.2 MHz to 0.8 MHz.

In a case where a difference between the natural frequencies of the transmission transducer and the reception transducer is smaller than 0.2 MHz, as described above, the reception transducer resonates when the ultrasonic waves are transmitted, and thereby a large amount of noise is contained in the output voltage. Thus, the reception accuracy is reduced in the reception transducer. By comparison, in a case where a difference between the natural frequencies of the transmission transducer and the reception transducer exceeds 0.8 MHz, a difference between the frequency of the ultrasonic waves transmitted from the transmission transducer and the frequency of the ultrasonic waves that is suitable to be received by the reception transducer increases, and thus the reception accuracy is reduced in the reception transducer.

In this respect, in this application example, the difference between the natural frequencies of the transmission transducer and the reception transducer is 0.2 MHz to 0.8 MHz. In this manner, while the noise component is reduced, it is possible for the reception transducer to receive reflected waves of the ultrasonic waves transmitted from the transmission transducer with high receiving sensitivity, and improvement in the transmission/reception efficiency of the ultrasonic waves is achieved in the ultrasonic device.

In the ultrasonic device according to the application example, it is preferable that the natural frequency of the reception transducer is lower than the natural frequency of the transmission transducer.

In this application example, the natural frequency of the reception transducer is lower than the natural frequency of the transmission transducer. In other words, in a case where the transmission transducer transmits the ultrasonic waves and the reception transducer receives the ultrasonic waves reflected from the target subject, the reflected ultrasonic waves are significantly attenuated, compared to the transmitted ultrasonic waves. Hence, in the ultrasonic measurement, it is necessary to increase the receiving sensitivity in the reception transducer. In this application example, the reception transducer has a low natural frequency. Note that the opening width of the second opening may be increased or the film thickness dimension of the receiving piezoelectric film may be decreased. In this manner, the second vibration portion in the reception transducer is likely to be bent, and thus it is possible to increase the receiving sensitivity.

An ultrasonic module according to an application example includes: an ultrasonic device that includes a substrate provided with a first opening and a second opening, a support film that is provided on the substrate and closes the first opening and the second opening, a transmitting piezoelectric film that is provided on the support film at a position which overlaps the first opening when viewed in a thickness direction of the substrate and that is sandwiched between a pair of electrodes in the thickness direction of the substrate, and a receiving piezoelectric film that is provided on the support film at a position which overlaps the second opening when viewed in the thickness direction of the substrate and that is sandwiched between a pair of electrodes in an intersecting direction intersecting with the thickness direction of the substrate; and a housing that accommodates the ultrasonic device. A film thickness dimension of the receiving piezoelectric film in the thickness direction of the substrate is smaller than a film thickness dimension of the transmitting piezoelectric film.

In this application example, as described above, it is possible to improve the transmission/reception efficiency of the ultrasonic device. Hence, it is possible to achieve the same operational effect also in the ultrasonic module that accommodates the ultrasonic device, and thus it is possible to improve the transmission/reception efficiency when a transmission/reception process of the ultrasonic waves is performed.

An ultrasonic measuring device according to an application example includes: an ultrasonic device that includes a substrate provided with a first opening and a second opening, a transmitting piezoelectric film that is provided on the support film at a position which overlaps the first opening when viewed in a thickness direction of the substrate and that is sandwiched between a pair of electrodes in the thickness direction of the substrate, and a receiving piezoelectric film that is provided on the support film at a position which overlaps the second opening when viewed in the thickness direction of the substrate and that is sandwiched between a pair of electrodes in an intersecting direction intersecting with the thickness direction of the substrate; and a controller that controls the ultrasonic device. A film thickness dimension of the receiving piezoelectric film in the thickness direction of the substrate is smaller than a film thickness dimension of the transmitting piezoelectric film.

In this application example, as described above, it is possible to improve the transmission/reception efficiency of the ultrasonic device. Hence, the controller controls the ultrasonic device, and thereby, through the transmission/reception process of the ultrasonic waves which has high transmission/reception efficiency, it is possible to realize the ultrasonic measurement with high accuracy. For example, in a case of acquiring an internal tomographic image of the target subject based on measurement results of the ultrasonic measurement, it is possible to acquire the internal tomographic image with high accuracy.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an ultrasonic measuring device of this embodiment will be described with reference to figures.

Configuration of Ultrasonic Measuring Device

Figure 1:
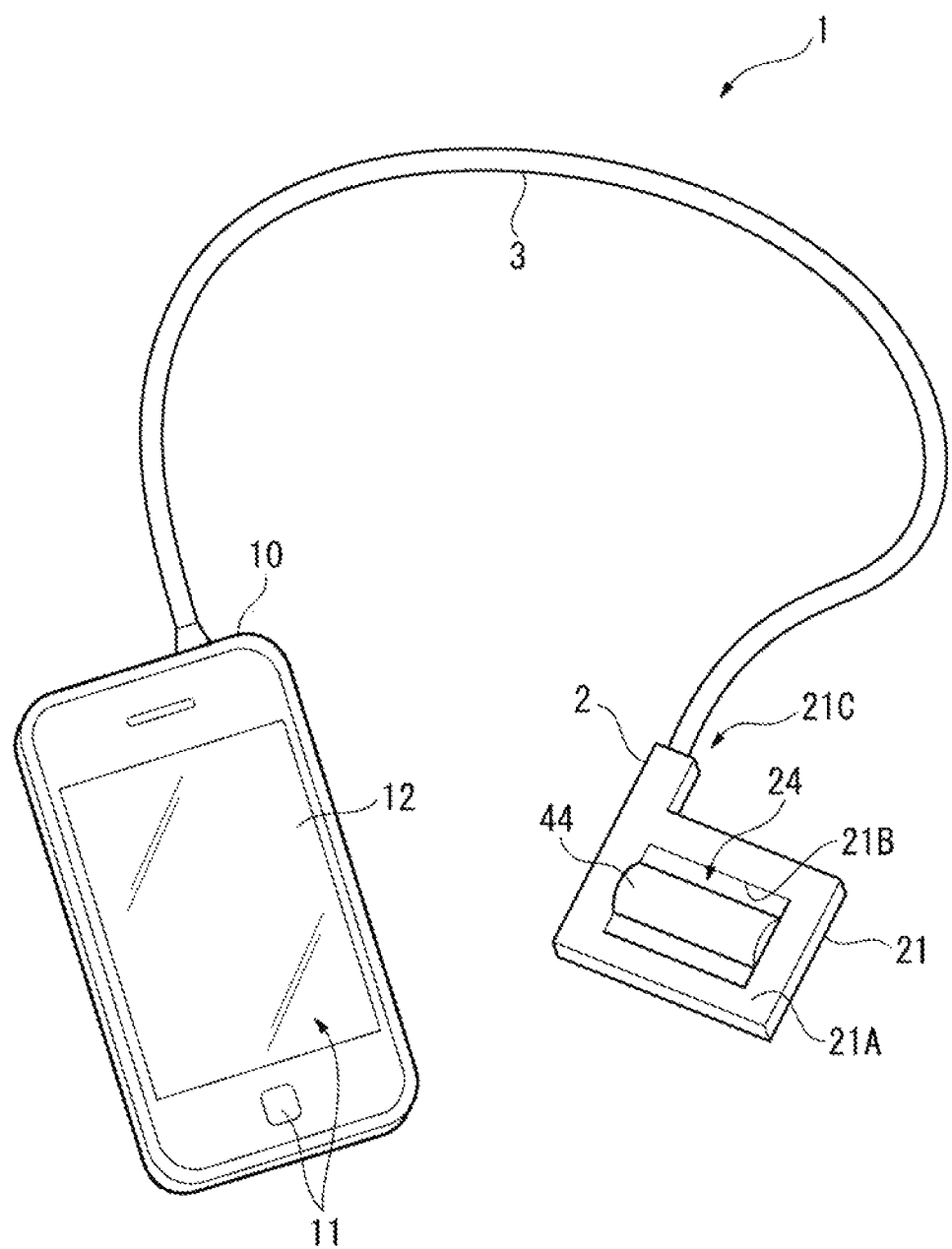
FIG. 1 is a perspective view illustrating a schematic configuration of an ultrasonic measuring device according to a first embodiment of the invention.
Figure 2:
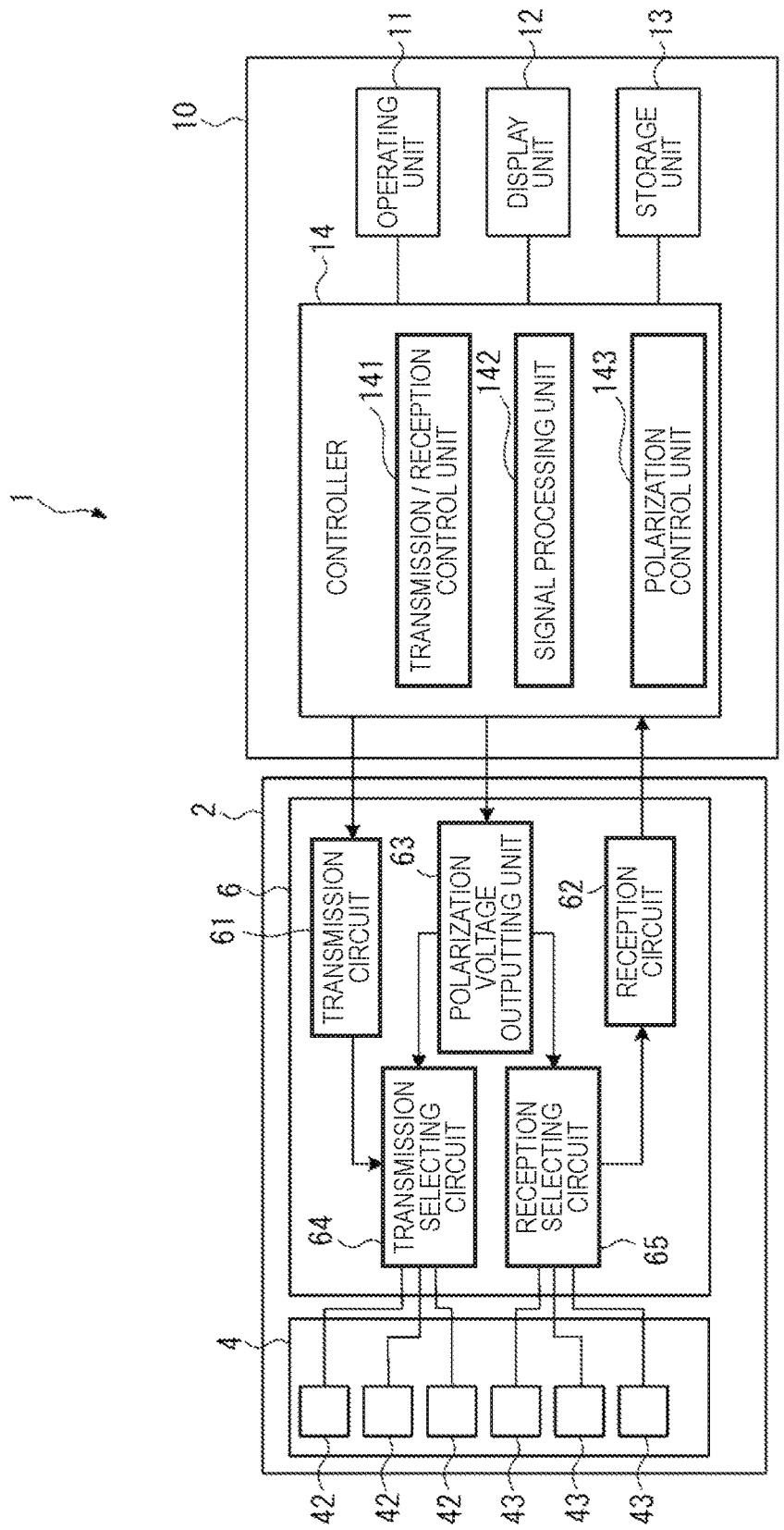
FIG. 2 is a block diagram illustrating a schematic configuration of the ultrasonic measuring device of the embodiment.

FIG. 1 is a perspective view illustrating a schematic configuration of an ultrasonic measuring device 1 according to the embodiment. FIG. 2 is a block diagram illustrating a schematic configuration of the ultrasonic measuring device 1 of the embodiment.

As illustrated in FIG. 1, the ultrasonic measuring device 1 of the embodiment includes an ultrasonic probe 2 and a control device 10 that is electrically connected to the ultrasonic probe 2 via a cable 3.

In the ultrasonic measuring device 1, the ultrasonic probe 2 comes into contact with a front surface of a target subject (for example, a living body), and ultrasonic waves are emitted into the living body from the ultrasonic probe 2. In addition, the ultrasonic waves reflected from an organ in the target subject (living body) is received by the ultrasonic probe 2 and, for example, an internal tomographic image of the inside of the living body is acquired, based on a received signal thereof or a state (for example, bloodstream or the like) of the organ in the living body is measured.

Configuration of Ultrasonic Probe

Figure 3:
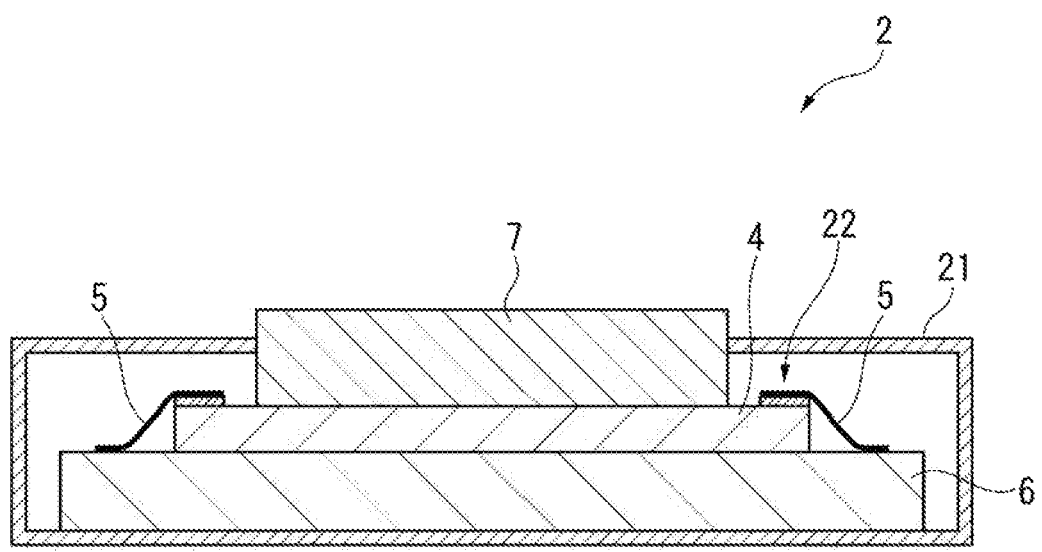
FIG. 3 is a sectional view illustrating a schematic configuration of an ultrasonic probe of the embodiment.

FIG. 3 is a sectional view illustrating a schematic configuration of the ultrasonic probe 2.

The ultrasonic probe 2 is an ultrasonic module and includes a housing 21 and an ultrasonic sensor 22.

Configuration of Housing

As illustrated in FIG. 1, the housing 21 is formed to have a box shape with a rectangular shape in plan view, and accommodates the ultrasonic sensor 22. One surface (sensor surface 21A) orthogonal to the thickness direction of the housing 21 is provided with a sensor window 21B through which a part (acoustic lens 7 which will be described below) of the ultrasonic sensor 22 is exposed. In addition, a part (side surface in an example illustrated in FIG. 1) of the housing 21 is provided with a through-hole, and the cable 3 is inserted into the housing 21 via the through-hole. Although not illustrated, the cable 3 is connected to the ultrasonic sensor 22 (circuit board 6 which will be described below) inside the housing 21.

Note that, in the embodiment, a configurational example in which the ultrasonic probe 2 and a control device 10 are connected to each other by using the cable 3 is employed; however, the embodiment is not limited thereto and, for example, the ultrasonic probe 2 and the control device 10 may be connected to each other through wireless communication, or various types of configurations of the control device 10 may be provided in the ultrasonic probe 2.

Configuration of Ultrasonic Sensor

As illustrated in FIG. 3, the ultrasonic sensor 22 includes an ultrasonic device 4, the circuit board 6, and the acoustic lens 7. As will be described below, the circuit board 6 is provided with a driver circuit or the like for controlling the ultrasonic device 4, and, the ultrasonic device 4 is electrically connected to the circuit board 6 via a wiring member 5 such as a flexible board. A surface of the ultrasonic device 4 on an ultrasonic transmission and reception side is provided with the acoustic lens 7, and the acoustic lens 7 is exposed outside from one surface side of the housing 21.

Configuration of Ultrasonic Device

Figure 4:
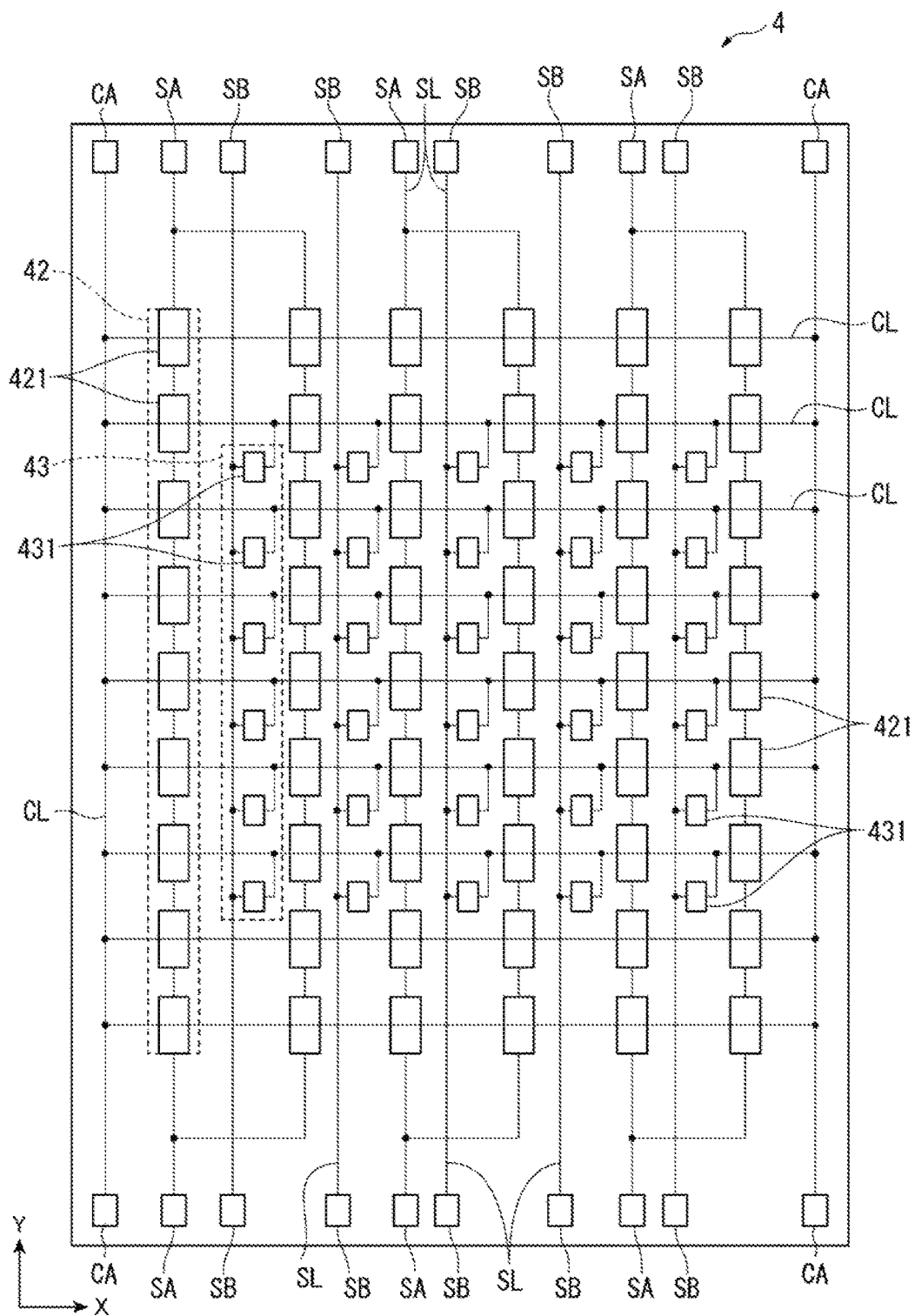
FIG. 4 is a plan view illustrating a schematic configuration of an ultrasonic device of the embodiment.

FIG. 4 is a plan view illustrating an example of the ultrasonic device 4.

In the following description, a scanning direction of the ultrasonic device 4 having a primary array structure as will be described below is referred to as an X direction, and a slice direction intersecting with (for example, in the embodiment, orthogonal to) the scanning direction is referred to as a Y direction.

The ultrasonic device 4 includes an ultrasonic transmitter 42, an ultrasonic receiver 43, a signal wire SL, a common electrode wire CL, a first signal terminal SA, a second signal terminal SB, and a common terminal CA.

The ultrasonic transmitter 42 has a plurality of transmission transducers 421 which are ultrasonic transducers for transmission, and the plurality of transmission transducers 421 are configured to be disposed in the Y direction. In addition, the ultrasonic receiver 43 has a plurality of reception transducers 431 which are ultrasonic transducers for reception, and the plurality of reception transducers 431 are configured to be disposed in the Y direction.

Note that, in the ultrasonic device 4 of the embodiment, the plurality of ultrasonic transmitters 42 and ultrasonic receivers 43 are alternately disposed in the X direction, and one set of ultrasonic transmitters 42 which are adjacent to each other in the X direction function as one transmission channel. In addition, each ultrasonic receiver 43 functions as one reception channel.

Figure 5:
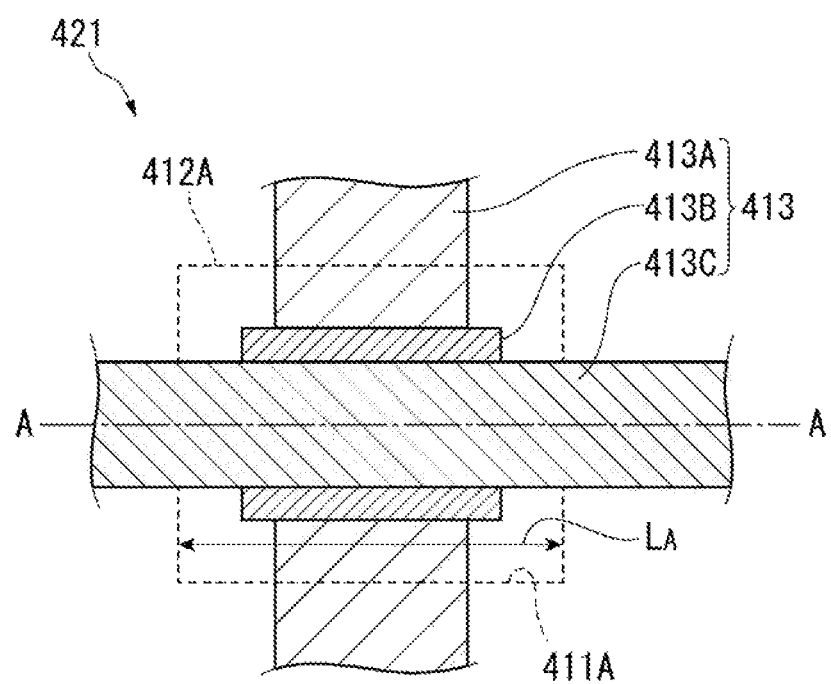
FIG. 5 is an enlarged plan view illustrating a transmission transducer of the embodiment.
Figure 6:
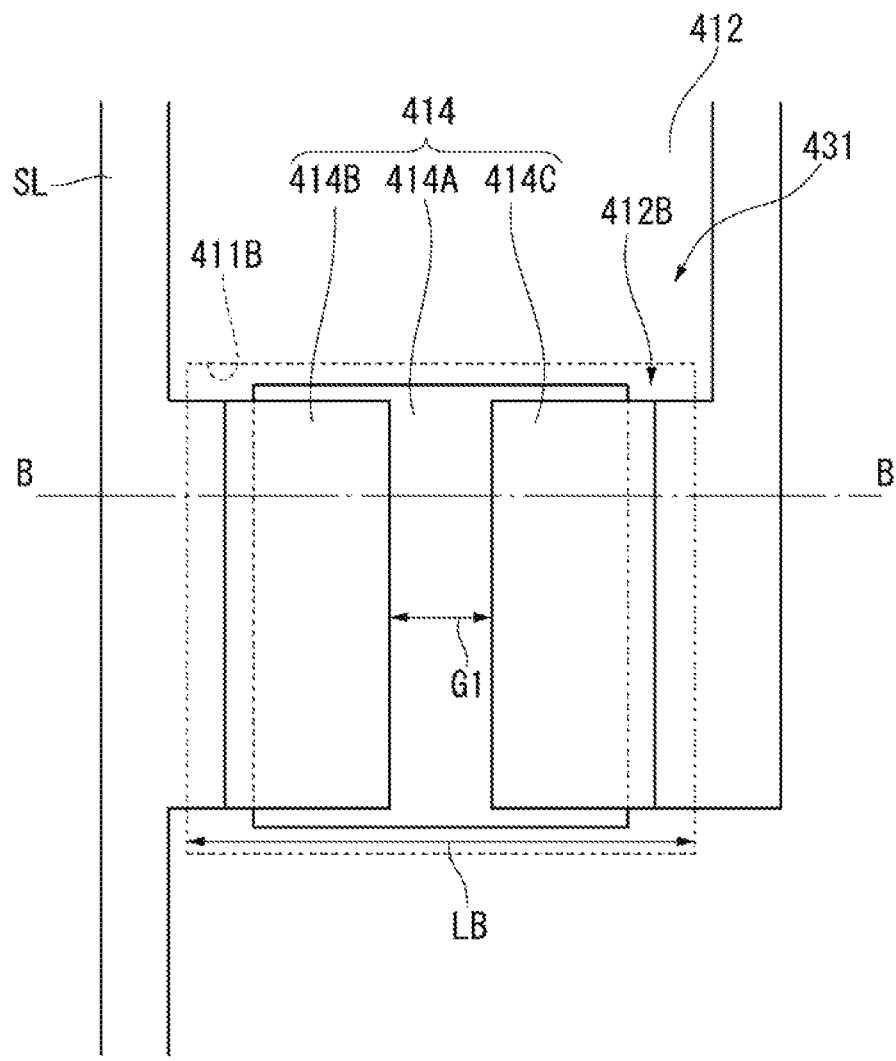
FIG. 6 is an enlarged plan view illustrating a reception transducer of the embodiment.
Figure 7:
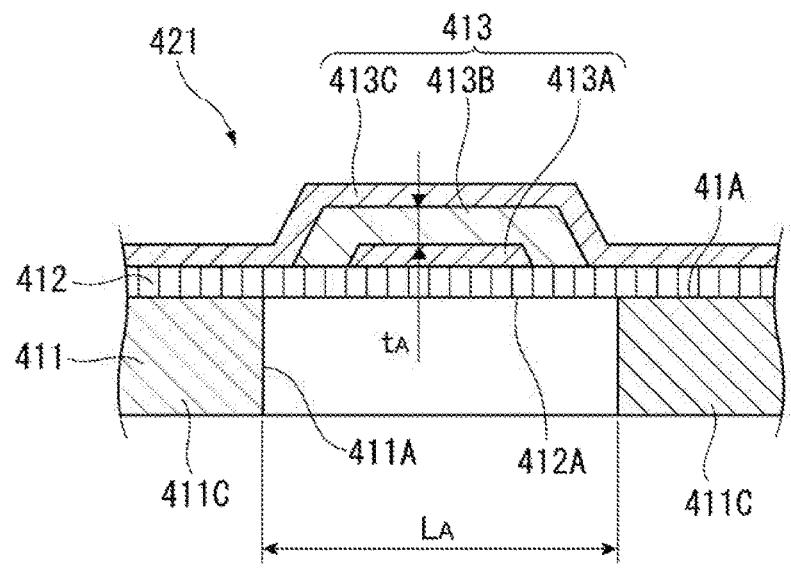
FIG. 7 is a sectional view illustrating the transmission transducer of the embodiment.
Figure 8:
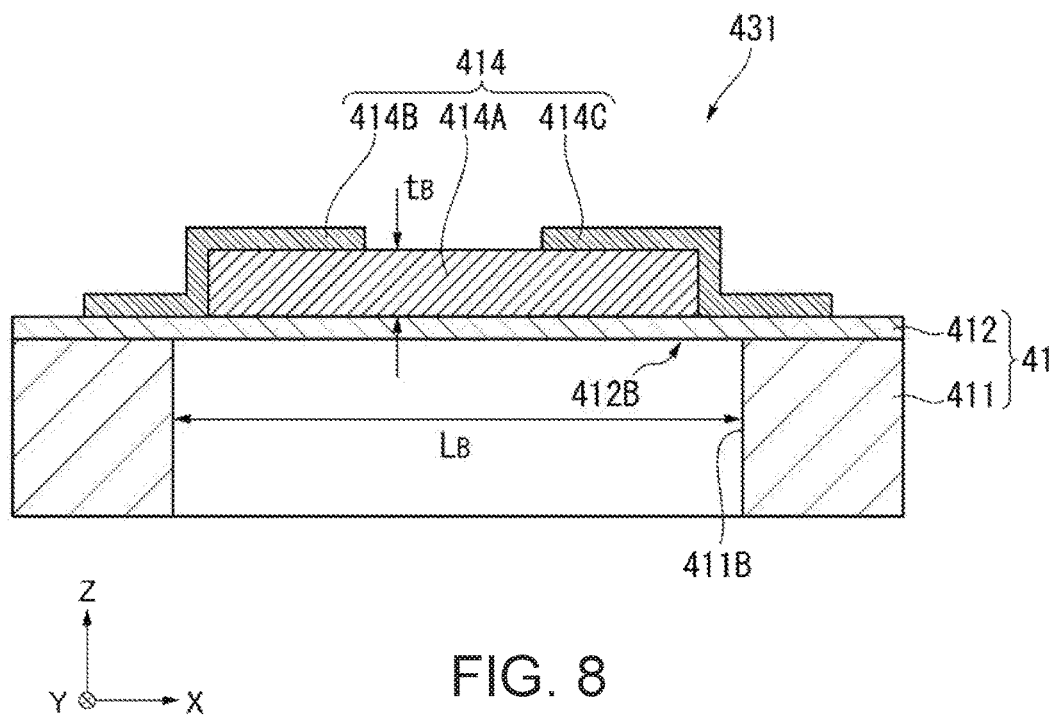
FIG. 8 is a sectional view illustrating the reception transducer of the embodiment.

FIG. 5 is an enlarged plan view illustrating the transmission transducer 421, and FIG. 6 is an enlarged plan view illustrating the reception transducer 431. In addition, FIG. 7 is an enlarged sectional view illustrating the transmission transducer 421 taken along line A-A in FIG. 5. FIG. 8 is an enlarged sectional view illustrating the reception transducer 431 taken along line B-B in FIG. 6.

As illustrated in FIGS. 7 and 8, the ultrasonic device 4 includes an element substrate 411, a support film 412 provided on the element substrate 411, a transmission piezoelectric element 413 provided on the support film 412, and a reception piezoelectric element 414 provided on the support film 412.

For example, the element substrate 411 is a semiconductor substrate made of Si or the like. The element substrate 411 is provided with a first opening 411A provided at a position that overlaps a disposed position of each transmission transducer 421 and a second opening 411B provided at a position that overlaps a disposed position of each reception transducer 431. The first opening 411A and the second opening 411B are closed with the support film 412 provided on a back surface 41A side of the element substrate 411. Note that an opening width (opening area) of the first opening 411A and the second opening 411B will be described below.

A plane orientation of the Si substrate may be any one of (100), (110), or (111). In addition, the element substrate 411 may be configured of a composite substrate such as silicon on insulator (SOI). Further, the element substrate 411 may be made of alumina, $Ga_2O_3$, or GaN.

For example, the support film 412 is configured of a single layer of $SiO_2$, a stacked body of $SiO_2$, $ZrO_2$, and yttrium-stabilized zirconium (YSZ), or the like, and is provided to cover the entire back surface 41A side of the element substrate 411. A thickness dimension of the support film 412 is sufficiently smaller than a thickness dimension of the element substrate 411. Young's modulus of $SiO_2$ is about 75 GPa. In addition, Young's modulus of $ZrO_2$ is about 200 GPa.

Here, as illustrated in FIGS. 5 and 7, when viewed in the thickness direction of the element substrate 411 and the support film 412, a region of the support film 412 that overlaps the first opening 411A (transmission transducer 421) configures a first vibration portion 412A. In addition, as illustrated in FIGS. 6 and 7, when viewed in the thickness direction of the element substrate 411 and the support film 412, a region of the support film 412 that overlaps the second opening 411B (reception transducer 431) configures a second vibration portion 412B. In other words, the first vibration portion 412A is supported by a partition portion 411C that surrounds the first opening 411A, and the second vibration portion 412B is supported by a partition portion 411C that surrounds the second opening 411B.

The transmission piezoelectric element 413 and the first vibration portion 412A that closes the first opening 411A together configure the transmission transducer 421.

As illustrated in FIGS. 5 and 7, the transmission piezoelectric element 413 is a stacked body of a lower electrode 413A, a transmitting piezoelectric film 413B, and an upper electrode 413C, and is provided on the first vibration portion 412A.

The lower electrode 413A configures one of a pair of electrodes by which the transmitting piezoelectric film 413B is sandwiched in the thickness direction of the element substrate 411, and the upper electrode 413C configures the other of the pair of electrodes.

The lower electrode 413A is formed to have a straight line shape in the Y direction, and is provided over the plurality of transmission transducers 421. Hence, the lower electrode 413A has the same potential in the transmission transducers 421 aligned in the Y direction. As illustrated in FIG. 4, the lower electrode 413A is connected to the corresponding first signal terminal SA disposed on the outer periphery of the support film 412 on ±Y sides, by the signal wire SL, and is electrically connected to the circuit board 6 in the first signal terminal SA.

In the embodiment, two ultrasonic transmitters 42 in the Y direction are included in one set and one transmission channel is formed. Accordingly, as illustrated in FIG. 4, the two adjacent ultrasonic transmitters 42 are connected to the first signal terminal SA.

The transmitting piezoelectric film 413B is formed of a thin film of a piezoelectric body such as lead zirconate titanate (PZT) and is configured to cover the lower electrode 413A on the first vibration portion 412A.

The upper electrode 413C is formed to have a straight line shape in the X direction, and is provided over the plurality of transmission transducers 421 which are aligned in the X direction. In addition, the upper electrodes 413C are connected to each other by the common electrode wire CL, is connected to the common terminal CA provided on the outer periphery (for example, ±Y sides) of the support film 412 (refer to FIG. 4), and is electrically connected to the circuit board 6 on the common terminal CA. Note that the common electrode wire CL is also connected to a second electrode 414C of the reception transducer 431. In other words, in the embodiment, the same common voltage is applied to the upper electrode 413C and the second electrode 414C which are connected to the common electrode wire CL.

The reception piezoelectric element 414 and the second vibration portion 412B that closes the second opening 411B together configure the reception transducer 431.

As illustrated in FIGS. 6 and 8, the reception piezoelectric element 414 is a stacked body of a receiving piezoelectric film 414A and a first electrode 414B and the second electrode 414C that are provided on the receiving piezoelectric film 414A, and the reception piezoelectric element 414 is provided on the second vibration portion 412B.

The first electrode 414B configures one of a pair of electrodes by which the receiving piezoelectric film 414A is sandwiched in an intersecting direction (in the embodiment, the X direction orthogonal to a Z direction) intersecting with the thickness direction of the element substrate 411, and the second electrode 414C configures the other of the pair of electrodes.

The receiving piezoelectric film 414A is formed of a thin film of the piezoelectric body, and is disposed on the second vibration portion 412B. The receiving piezoelectric film 414A is preferably made of a perovskite type transition metal oxide, and more preferably, similar to the transmitting piezoelectric film 413B, made of the perovskite type transition metal oxide containing Pb such as PZT, Zr, and Ti. Note that a material of the receiving piezoelectric film 414A is not limited to PZT, and may include a Pb-free material such as BiFeMnO$_3$—BaTiO$_3$ or KNaNbO$_3$. Young' modulus of the PZT used for the transmitting piezoelectric film 413B or the receiving piezoelectric film 414A is about 80 GPa in the thin film. The receiving piezoelectric film 414A made of such a perovskite type transition metal oxide (particularly, PZT) has particularly high piezoelectric property (piezoelectric e constant), and a large electric signal is output when the receiving piezoelectric film 414A is deformed.

Values of a piezoelectric constant $e_{ij}$, relative permittivity $\varepsilon_{ij}$, stiffness $C_{ij}$ of a piezoelectric body PZT used in simulation of this specification employ data of PZT-5H. PZT of the thin film (film formed through sputtering or the like) is known to have substantially the same physical constant as that of PZT of a bulk (large-sized solid cut out from a sintered body).

The first electrode 414B is disposed on a −X side to extend to the −X side on the top surface (end surface on a −Z side) of the receiving piezoelectric film 414A. In addition, as illustrated in FIG. 4, the first electrodes 414B included in the ultrasonic receiver 43 which configures one reception channel are connected to each other by the signal wire SL. The signal wire SL connected to the first electrode 414B is connected to the corresponding second signal terminal SB disposed on the outer periphery of the support film 412 of the element substrate 411 on ±Y sides, and is electrically connected to the circuit board 6 in the second signal terminal SB.

The second electrode 414C is disposed on a +X side to extend to the +X side on the top surface of the receiving piezoelectric film 414A. The front end of the second electrode 414C extends in the Y direction and is connected to the common electrode wire CL. Accordingly, similar to the upper electrode 413C of the transmission transducer 421, the common voltage is applied to the second electrode 414C.

The lower electrode 413A, the upper electrode 413C, the first electrode 414B, and the second electrode 414C are preferably made of one or a plurality of materials of Ti, Ir, TiO$_2$, IrO$_2$, Pt, in terms of conductivity, stability of the materials, and thin film stress to PZT. In addition, Young's moduli of the electrodes 413A, 413C, 414B, and 414C are about 200 GPa.

In the ultrasonic device 4 having such a configuration, a rectangular voltage having a predetermined frequency is applied between the lower electrode 413A and the upper electrode 413C, and thereby the first vibration portion 412A is vibrated such that the ultrasonic waves are transmitted from the transmission transducer 421. In addition, when the second vibration portion 412B is vibrated due to the ultrasonic waves reflected from the living body, an output voltage is output from the first electrode 414B, by which the receiving piezoelectric film 414A is sandwiched, in response to a distortion amount of the receiving piezoelectric film 414A, and the reception of the ultrasonic waves is detected.

In addition, although omitted in the figures, a reinforcing plate is disposed on a side of the support film 412 opposite to the element substrate 411. For example, the reinforcing plate is bonded, with a resin layer or the like, to the support film 412 positioned on the partition portion 411C of the element substrate 411, and reinforces the element substrate 411 and the support film 412.

Further, the first opening 411A and the second opening 411B of the element substrate 411 is filled with an acoustic matching layer made of silicone or the like, and the acoustic lens 7 is provided on the acoustic matching layer.

Dimension of Transmission Transducer and Reception Transducer

Next, dimensions of the transmission transducer 421 and the reception transducer 431 described above, will be described below.

Note that, in the following description, FIGS. 9 to 17 shows results calculated, based on a finite element method by using COMSOL Multiphysics (registered trademark: COMSOL Inc.). In the COMSOL Multiphysics, structure calculation and piezoelectric calculation are performed by being coupled as multiphysics.

Figure 9:
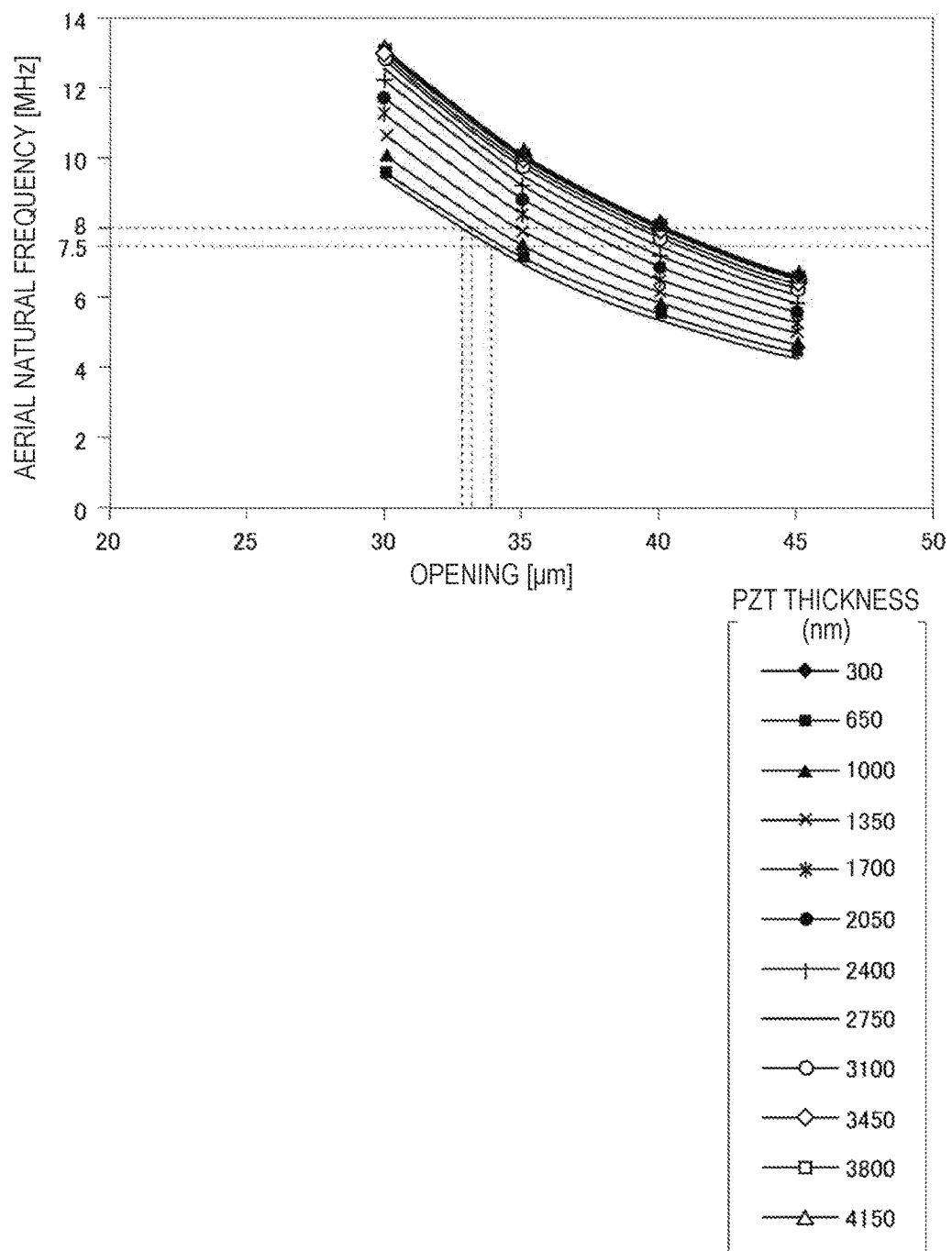
FIG. 9 is a graph illustrating a relationship between an opening width of an opening of an ultrasonic transducer and a natural frequency of the ultrasonic transducer.

FIG. 9 is a graph illustrating a relationship between an opening width of an opening (the first opening 411A or the second opening 411B) of the ultrasonic transducer and a natural frequency (frequency of the ultrasonic waves that can be transmitted and received) of the ultrasonic transducer.

In general, the frequency of the ultrasonic waves obtained in a case where the ultrasonic measurement is performed on the living body is about 2.5 MHz to 10 MHz. As illustrated in FIG. 9, in a case where ultrasonic waves having frequencies of 2.5 MHz to 10 MHz described above are transmitted or received by the ultrasonic transducer (the transmission transducer 421 or the reception transducer 431), the opening width (width dimension in a short axis direction) corresponding to the frequencies is about 30 μm to 45 μm. Hence, in the following description, characteristics of the transmission transducer 421 and the reception transducer 431 obtained in a case where the opening widths of the first opening 411A and the second opening 411B are changed in a range of 30 μm to 45 μm will be described.

Figure 10:
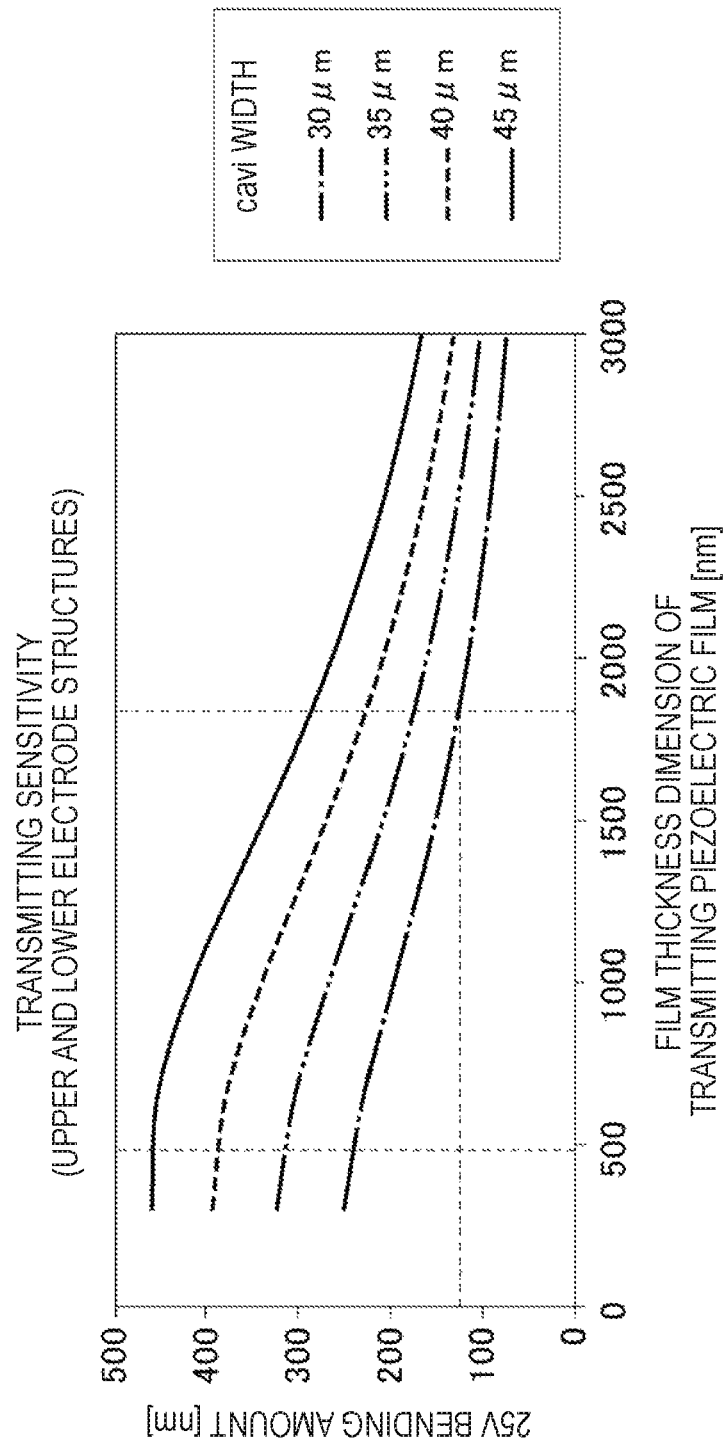
FIG. 10 is a graph illustrating a relationship between a film thickness dimension of a transmitting piezoelectric film and transmitting sensitivity in the transmission transducer.

FIG. 10 is a graph illustrating a relationship between the film thickness dimension of the transmitting piezoelectric film 413B and transmitting sensitivity in the transmission transducer 421. Note that the transmitting sensitivity described here indicates a distortion amount (bending amount (nm) in an opening direction, that is, the thickness direction of the support film 412) of the transmitting piezoelectric film 413B obtained when a predetermined drive voltage (for example, 25 V) is applied between the lower electrode 413A and the upper electrode 413C.

FIG. 10 is a simulation result obtained through the finite element method. When $t_A$ represents the film thickness dimension of the transmitting piezoelectric film 413B, $V_1$ represents a drive voltage that is applied between the lower electrode 413A and the upper electrode 413C, ε represents permittivity (permittivity of the transmitting piezoelectric film) between the electrodes, and e represents a piezoelectric constant of the transmitting piezoelectric film 413B, it is possible to qualitatively express, in $\eta = \varepsilon (V_1/t_A)e$, a distortion amount η (transmitting sensitivity) of the transmitting piezoelectric film 413B which is obtained when the drive voltage $V_1$ is applied. A physically more accurate distortion amount η (transmitting sensitivity) of the transmitting piezoelectric film 413B, which is obtained when the drive voltage $V_1$ is applied, is obtained as FIG. 10 through simulation of multiphysics by the finite element method.

Hence, the more the film thickness dimension $t_A$ increases, the lower the transmitting sensitivity is. Here, it is not preferable that the film thickness dimension $t_A$ is smaller than 300 nm, because there is a possibility that dielectric breakdown occurs due to the application of the polarization voltage or the drive voltage during the polarization process.

In other words, in the transmission transducer 421, for example, a film of the lower electrode 413A having a stacked structure of Pt and Ir oxide is formed on the support film 412 (for example, $ZrO_2$), and a film of the transmitting piezoelectric film 413B made of PZT is formed thereon. Here, heating is performed at a temperature above or below 700° C. during the film formation and burning of PZT. At this time, there is an occurrence of a phenomenon in which Pb atoms of PZT are dispersed to the lower electrode 413A side. The dispersion of the Pb atoms is stopped on an interface between the lower electrode 413A and the support film 412 ($ZrO_2$); however, Pb defects occur in an entire region in PZT (transmitting piezoelectric film 413B). The Pb defects result in the oxygen defects and, for example, the oxygen defects are leak paths when the polarization voltage is applied to the transmitting piezoelectric film 413B and the polarization treatment is performed. Thus, hopping conduction of electrons increases, and there is a concern that, finally, the dielectric breakdown will occur and the withstand voltage will be reduced. In order to reduce the dielectric breakdown, the film thickness dimension $t_A$ of the transmitting piezoelectric film 413B is preferably 300 nm or larger. In addition, in a case where the transmitting piezoelectric film 413B is actually formed, it is necessary to consider variations during manufacturing. Hence, in order to secure pressure resistance in consideration of manufacturing margin, as illustrated in FIG. 10, the film thickness dimension $t_A$ is preferably larger than 500 nm.

By comparison, in a case where the film thickness dimension exceeds 1800 nm, it is difficult for the first vibration portion 412A to be bent due to an influence of the stiffness of the transmitting piezoelectric film 413B (decrease in transmitting sensitivity). In particular, in the ultrasonic measuring device 1, the ultrasonic waves transmitted from the transmission transducer 421 are attenuated in the living body, and the reflected ultrasonic waves, which are attenuated, are received by the reception transducer 431. In this case, as the transmitting sensitivity of the transmission transducer 421, the bending amount of the first vibration portion 412A is preferably secured to be larger than at least about 120 nm. In a case where the opening width of the first opening 411A is 30 μm such that the transmitting sensitivity is the lowest level, in order to satisfy the conditions described above, the film thickness dimension of the transmitting piezoelectric film 413B is preferably 1800 nm or smaller.

In other words, in the embodiment, the transmitting piezoelectric film 413B preferably has the film thickness dimension $t_A$ in a range of 300 nm to 1800 nm, and more preferably in a range of 500 nm to 1800 nm.

Figure 11:
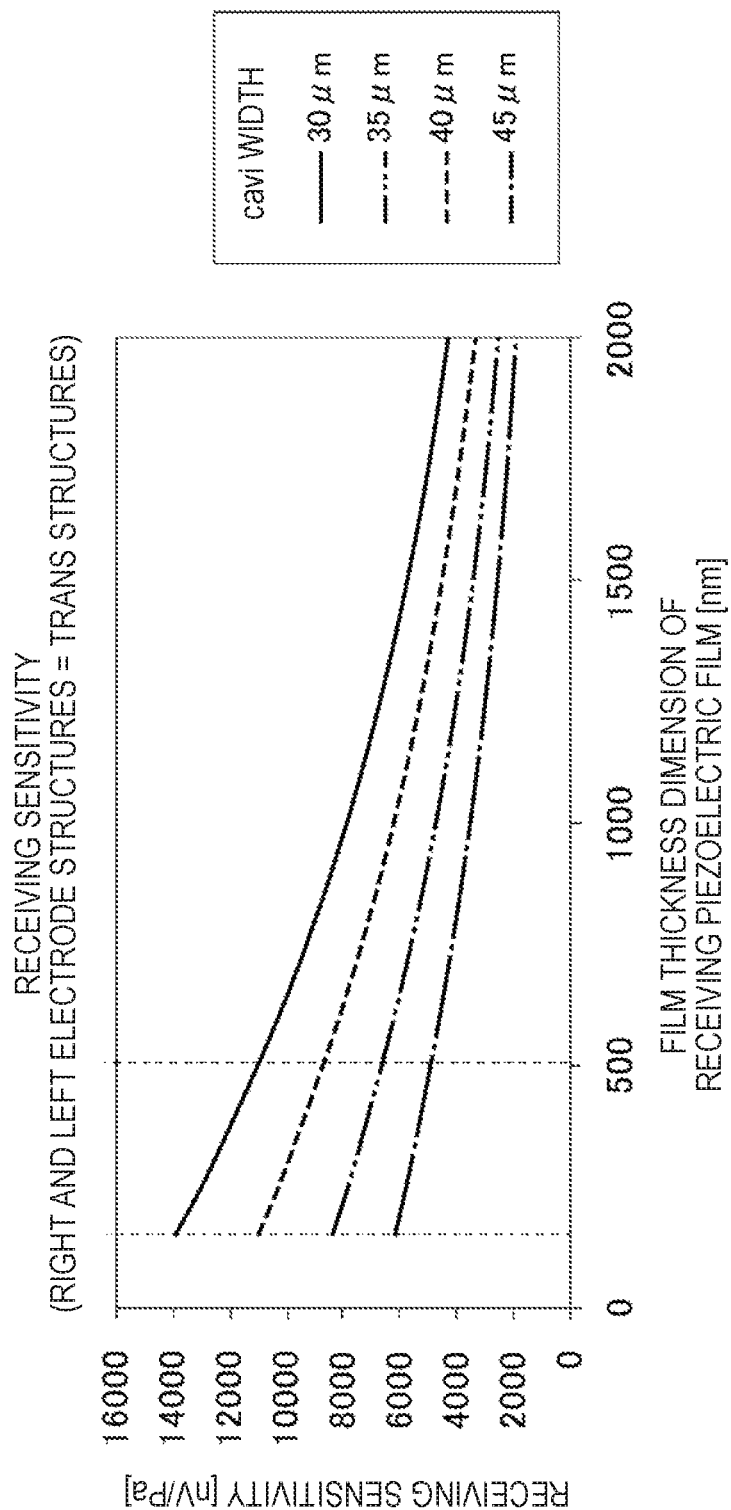
FIG. 11 is a graph illustrating a relationship between a film thickness dimension of a receiving piezoelectric film and receiving sensitivity in the reception transducer.

FIG. 11 is a graph illustrating the receiving sensitivity obtained through the simulation of multiphysics using the finite element method. FIG. 11 illustrates a relationship between a film thickness dimension of the receiving piezoelectric film 414A and receiving sensitivity (nV/Pa) in the reception transducer 431.

When η represents the distortion amount of the receiving piezoelectric film 414A, g represents a distance of a gap G1 (refer to FIG. 6) between electrodes, ε represents permittivity (permittivity of the receiving piezoelectric film) between the electrodes, and e represents a piezoelectric constant of the receiving piezoelectric film 414A, an output voltage $V_2$ that is output from the first electrode 414B in the reception transducer 431 is qualitatively expressed in $V_2=\eta g e/\varepsilon$. In other words, in a case where the stiffness of the receiving piezoelectric film 414A is not taken into consideration, it is obvious that the receiving sensitivity is constant regardless of the film thickness dimension $t_B$ of the receiving piezoelectric film 414A.

However, when the film thickness dimension $t_B$ increases, the stiffness of the second vibration portion 412B increases, and thus it is difficult for the second vibration portion to be bent. Accordingly, as illustrated in FIG. 11, regarding the receiving sensitivity of the reception transducer 431, the receiving sensitivity decreases as the film thickness dimension $t_B$ increases.

Incidentally, the reflected ultrasonic waves, which are attenuated, are received in the reception transducer 431, the receiving sensitivity of at least 5,000 (nV/Pa) or higher may be obtained. As illustrated in FIG. 11, in a case where the film thickness dimension $t_B$ of the receiving piezoelectric film 414A is 500 nm or smaller, it is possible to satisfy the conditions described above, and the reception transducer 431 having appropriate reception efficiency is obtained.

In addition, in a case where the film thickness dimension $t_B$ exceeds 500 nm, it is difficult for the second vibration portion 412B to be bent due to an influence of the stiffness of the receiving piezoelectric film 414A, and thus the receiving sensitivity decreases.

In addition, in the polarization process in the reception transducer 431, the polarization voltage is applied between the first electrode 414B and the second electrode 414C. Here, in the embodiment, since the receiving piezoelectric film 414A is formed of the thin film, the gap G1 between the first electrode 414B and the second electrode 414C is sufficiently increased, compared to the film thickness dimension $t_B$ of the receiving piezoelectric film 414A and is, for example, 5 μm. In addition, since the receiving piezoelectric film 414A has the PZT formed on the support film 412, an electrode layer that absorbs the Pb atoms is not interposed between films, unlike the transmission piezoelectric element 413. Accordingly, the dispersion of the Pb atoms is reduced from the PZT, and thus Pb dispersion or the oxygen defects due to the dispersion is reduced. In other words, the withstand voltage of the receiving piezoelectric film 414A increases, compared to the transmitting piezoelectric film 413B.

However, also in the receiving piezoelectric film 414A, when the film thickness dimension $t_B$ is smaller than 80 nm, dispersion of the Pb atoms in the film formation atmosphere during the film formation of the receiving piezoelectric film 414A and the oxygen defects due to the dispersion are likely to occur. In order to reduce the defects, the film thickness dimension $t_B$ of the receiving piezoelectric film 414A is preferably 80 nm or larger. In addition, in order to secure the pressure resistance in consideration of manufacturing margin, the film thickness dimension is preferably 150 nm or larger.

In other words, the film thickness dimension $t_B$ of the receiving piezoelectric film 414A is preferably 80 nm to 500 nm, and more preferably 150 nm to 500 nm.

Incidentally, the ultrasonic device 4 performs a transmission process of the ultrasonic waves by the transmission transducer 421 and performs a reception process of the ultrasonic waves by the reception transducer 431. Therefore, even when only the characteristics of any one process are appropriate, the transmission/reception efficiency decreases in a case where the other is not appropriate.

Here, the inventor of the invention finds that a product of the transmitting sensitivity in the transmission transducer 421 and the receiving sensitivity in the reception transducer 431 is defined as a figure of merit of the transmission/reception process in the ultrasonic device, and, in order to perform the transmission/reception process with high accuracy, the figure of merit needs to be 750,000 or larger.

Figure 12:
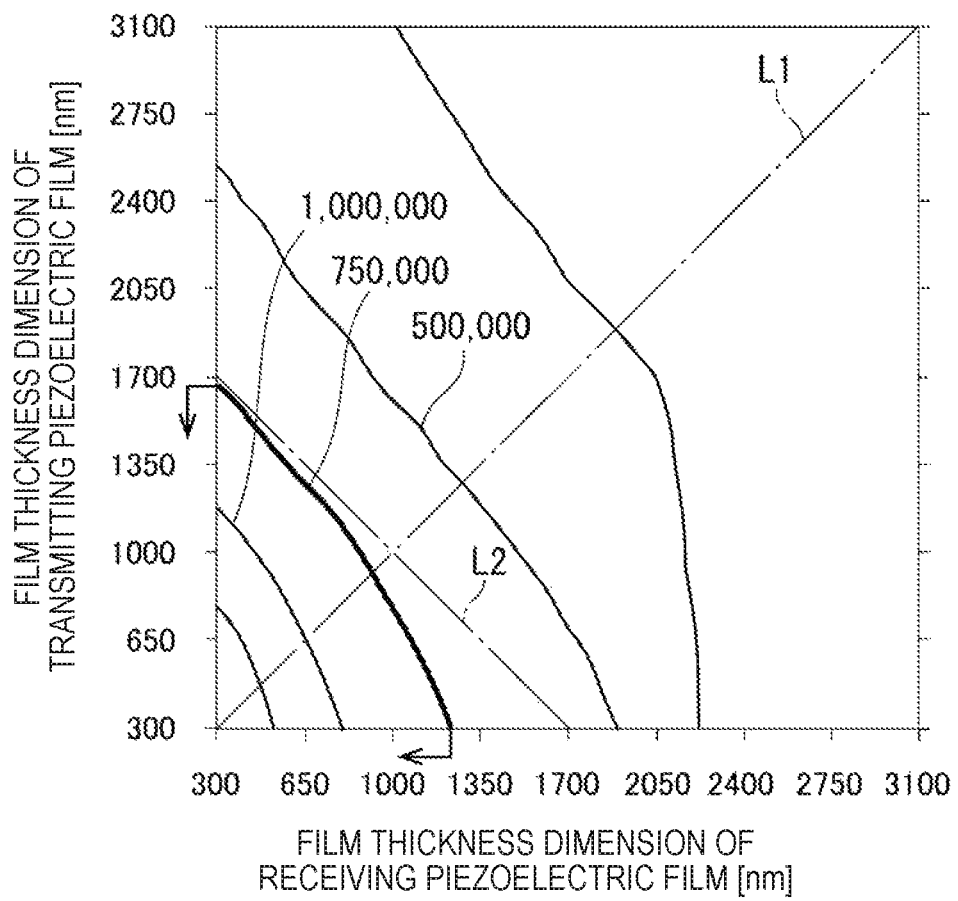
FIG. 12 is a graph illustrating a relationship between a film thickness dimension of the transmitting piezoelectric film, a film thickness dimension of the receiving piezoelectric film, and a figure of merit when a first opening and a second opening is 30 μm.
Figure 13:
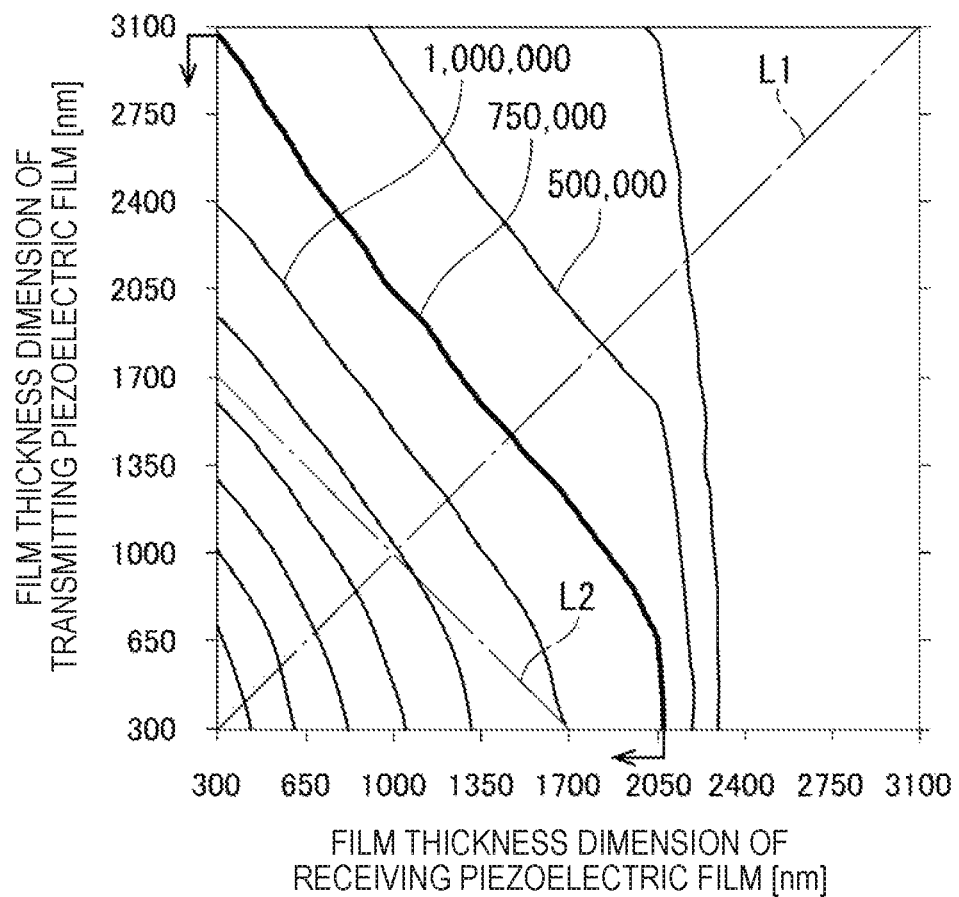
FIG. 13 is a graph illustrating a relationship between the film thickness dimension of the transmitting piezoelectric film, the film thickness dimension of the receiving piezoelectric film, and the figure of merit when the first opening and the second opening is 35 μm.
Figure 14:
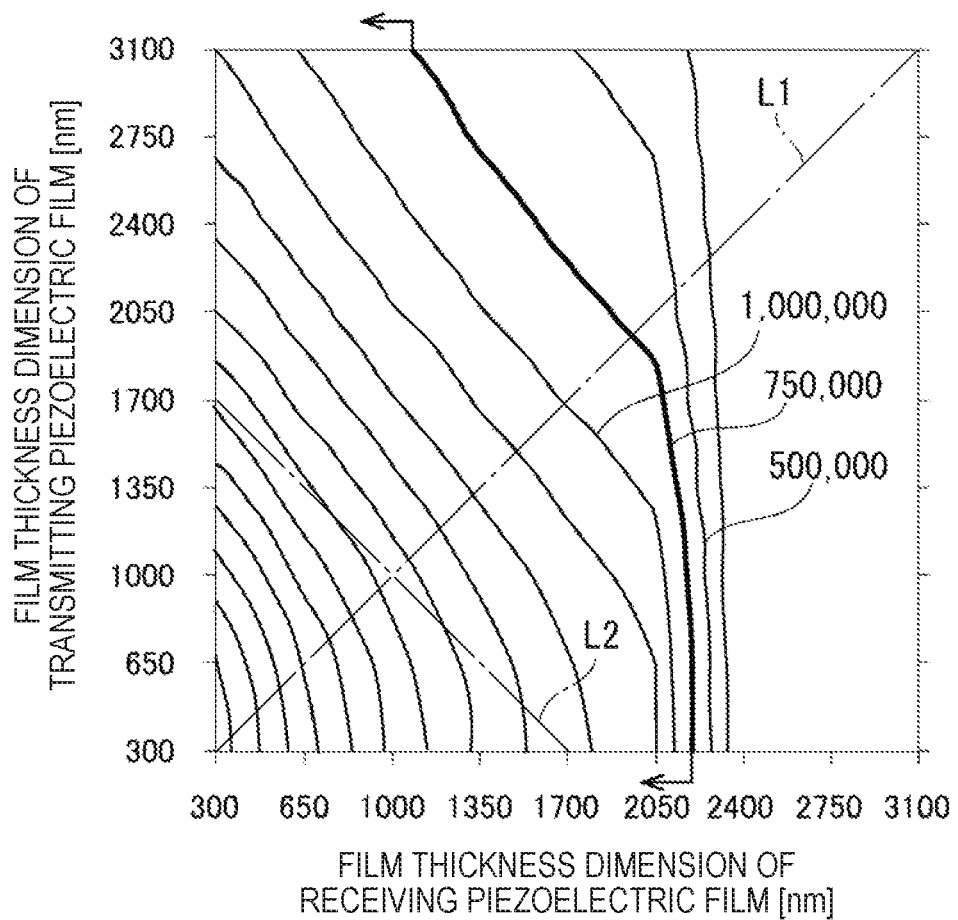
FIG. 14 is a graph illustrating a relationship between the film thickness dimension of the transmitting piezoelectric film, the film thickness dimension of the receiving piezoelectric film, and the figure of merit when the first opening and the second opening is 40 μm.
Figure 15:
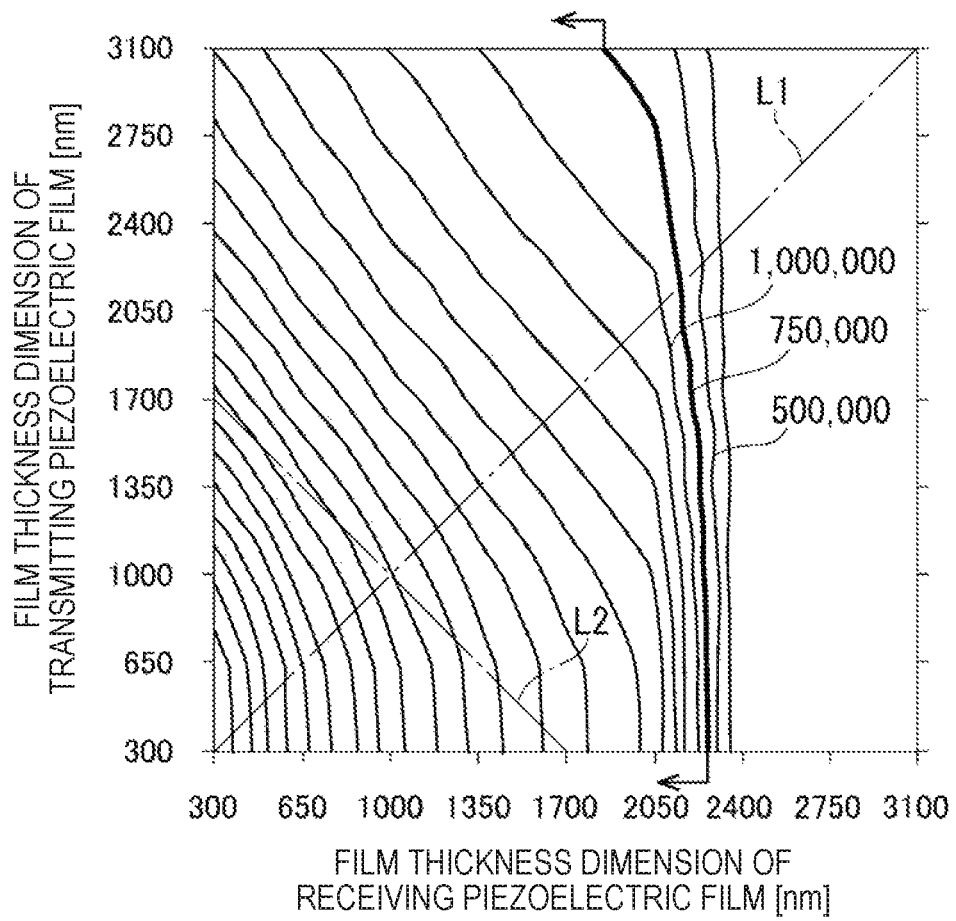
FIG. 15 is a graph illustrating a relationship between the film thickness dimension of the transmitting piezoelectric film, the film thickness dimension of the receiving piezoelectric film, and the figure of merit when the first opening and the second opening is 45 μm.

FIG. 12 is a graph illustrating a relationship between the film thickness dimension $t_A$ of the transmitting piezoelectric film 413B, the film thickness dimension $t_B$ of the receiving piezoelectric film 414A, and the figure of merit when the first opening 411A and the second opening 411B are 30 μm. FIG. 13 is a graph illustrating a relationship between the film thickness dimension $t_A$ of the transmitting piezoelectric film 413B, the film thickness dimension $t_B$ of the receiving piezoelectric film 414A, and the figure of merit when the first opening 411A and the second opening 411B are 35 μm. FIG. 14 is a graph illustrating a relationship between the film thickness dimension $t_A$ of the transmitting piezoelectric film 413B, the film thickness dimension $t_B$ of the receiving piezoelectric film 414A, and the figure of merit when the first opening 411A and the second opening 411B are 40 μm. FIG. 15 is a graph illustrating a relationship between the film thickness dimension $t_A$ of the transmitting piezoelectric film 413B, the film thickness dimension $t_B$ of the receiving piezoelectric film 414A, and the figure of merit when the first opening 411A and the second opening 411B are 45 μm. Note that contour lines in FIGS. 12 to 15 are divided by unit of the figure of merit of 250,000, and have a large value as the contour lines are closer to the left side. In addition, the contour line represented by the thick line indicates that the figure of merit is 750,000.

Figure 16:
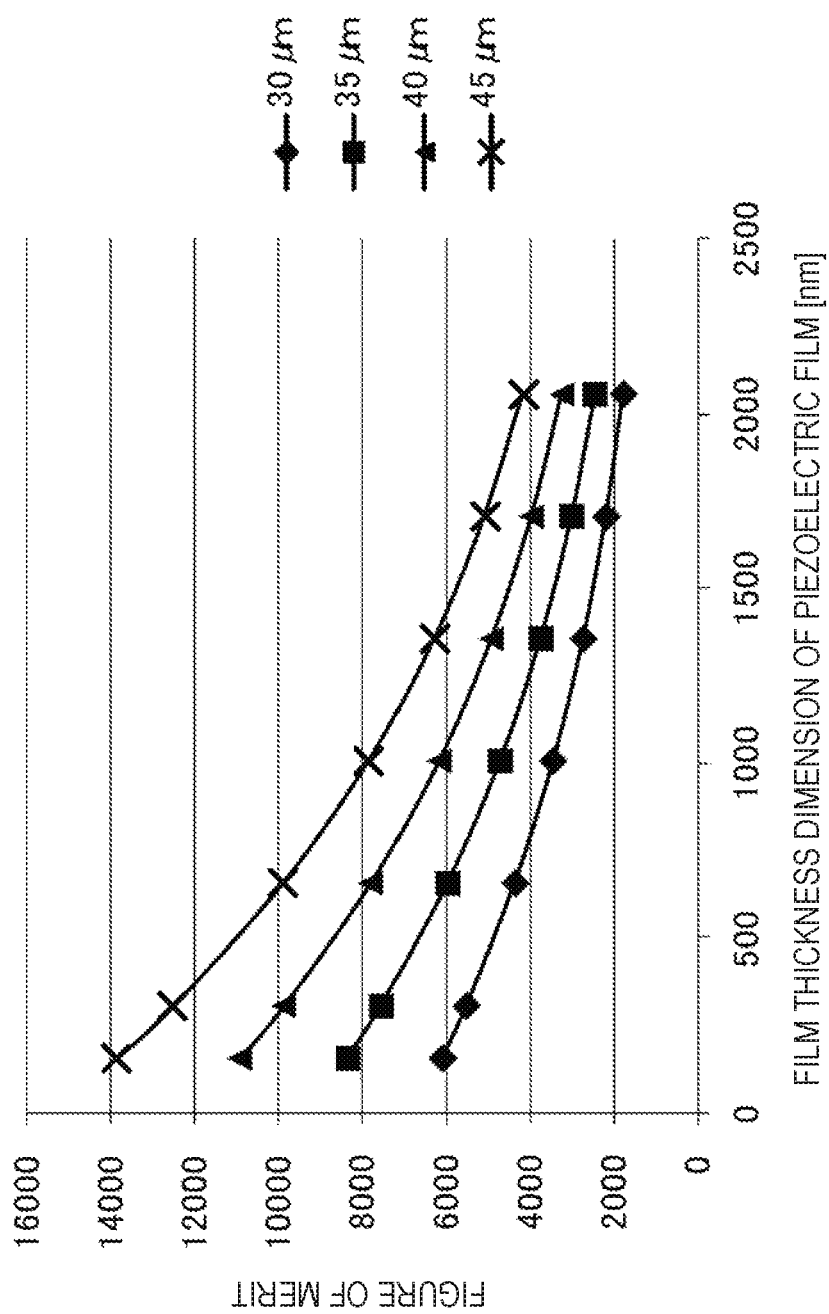
FIG. 16 is a graph illustrating a figure of merit of the ultrasonic transducer in an example of related art.

In addition, FIG. 16 is a graph illustrating a figure of merit of the ultrasonic transducer in an example of related art. As the example of the related art, an example in which the transmission and reception of the ultrasonic waves are performed (the film thickness dimension $t_A$ of the transmitting piezoelectric film 413B is the same as the film thickness dimension $t_B$ of the receiving piezoelectric film 414A), by using an ultrasonic transducer having the same configuration (stacking of the lower electrode, the piezoelectric film, and the upper electrode on the support film) as that of the transmission transducer 421 is employed.

Here, as in the example in the related art illustrated in FIG. 16, in a case where the film thickness dimension $t_A$ of the transmitting piezoelectric film 413B is the same value as the film thickness dimension $t_B$ of the receiving piezoelectric film 414A, it is not possible to have the figure of merit of 750,000.

However, as illustrated in FIGS. 12 to 15, in the embodiment, the figure of merit increases as the opening widths of the first opening 411A and the second opening 411B increase. In addition, also in a case where the opening widths of the first opening 411A and the second opening 411B are 30 μm (case of having the lowest figure of merit), the film thickness dimension $t_A$ of the transmitting piezoelectric film 413B is 300 nm to 1800 nm, and the ultrasonic device 4, of which the figure of merit exceeds 750,000 is obtained when the film thickness dimension $t_B$ of the receiving piezoelectric film 414A is in a range of 80 nm to 500 nm.

In addition, in FIGS. 12 to 15, when a line (dot-and-dash line L2) orthogonal to a line (dot-and-dash line L1) in which $t_A = t_B$ is pulled, absolute values of slopes of contour lines are larger than the absolute value of the slope of the dot-and-dash line L2. In other words, the contour lines are inclined with respect to a direction parallel to the vertical axis. This means that the figure of merit has a strong tendency to increase when the film thickness dimension $t_B$ of the receiving piezoelectric film 414A decreases. In other words, the film thickness dimension $t_B$ of the receiving piezoelectric film 414A is smaller than the film thickness dimension $t_A$ of the transmitting piezoelectric film 413B ($t_A < t_B$), and thereby the figure of merit tends to more increase.

Incidentally, as illustrated in FIG. 9, in a case where the natural frequency of the ultrasonic transducer is set to a predetermined value, the more the film thickness dimension increases, the higher the natural frequency, and the more the film thickness dimension decreases, the lower the natural frequency is, also depending on the film thickness dimension of the piezoelectric film (the transmitting piezoelectric film 413B or the receiving piezoelectric film 414A) that configures the corresponding ultrasonic transducer.

Here, in the ultrasonic device 4, in order to perform the transmission/reception process of the ultrasonic waves having the predetermined frequency, the natural frequency of the transmission transducer 421 needs to be substantially the same as the natural frequency of the reception transducer 431. Here, as described above, it is advantageous to configure the ultrasonic device 4 having high performance when the film thickness dimension $t_A$ of the transmitting piezoelectric film 413B is smaller than the film thickness dimension $t_B$ of the receiving piezoelectric film 414A. Accordingly, in the embodiment, an opening width $L_A$ of the first opening 411A that overlaps the transmission transducer 421 is formed to be smaller than an opening width $L_B$ of the second opening 411B that overlaps the reception transducer 431.

For example, the film thickness dimension $t_A$ of the transmitting piezoelectric film 413B is 650 nm when the transmission/reception process of the ultrasonic waves of 8 MHz is performed, and the opening width $L_A$ of the first opening 411A is about 32.8 μm in a case where the film thickness dimension $t_B$ of the receiving piezoelectric film 414A is 300 nm. Thus, the opening width $L_B$ of the second opening is about 33.4 μm.

However, when the transmission transducer 421 and the reception transducer 431 have the same natural frequency as each other, and the ultrasonic waves are transmitted from the transmission transducer 421, the reception transducer 431 resonates, and an output voltage in response to the resonance is output from the reception transducer 431 and is the noise component.

Hence, in the embodiment, the natural frequency of the transmission transducer 421 is set to a value different from the natural frequency of the reception transducer 431. Specifically, the natural frequency of the reception transducer 431 is set to be smaller preferably by a range of 0.2 MHz to 0.8 MHz than the natural frequency of the transmission transducer 421, and is set to be smaller more preferably by 0.5 MHz than the natural frequency of the reception transducer 431.

For example, in the transmission/reception process of the ultrasonic waves of 8 MHz, in a case where the natural frequency of the transmission transducer 421 is set to 8 MHz, the natural frequency of the reception transducer 431 is set to 7.5 MHz. Hence, the film thickness dimension $t_A$ of the transmitting piezoelectric film 413B is 650 nm. Thus, the opening width $L_A$ of the first opening 411A is about 32.8 μm, and the opening width $L_B$ of the second opening 411B is about 34.0 μm in a case where the film thickness dimension $t_B$ of the receiving piezoelectric film 414A is 300 nm.

In this case, the opening width $L_B$ of the second opening 411B corresponding to the reception transducer 431 increases, and the receiving sensitivity is improved because the second vibration portion 412B is easily vibrated.

In the ultrasonic device 4 of the embodiment, a natural frequency $f_A$ of the transmission transducer 421 is set in proportion to a frequency of the ultrasonic waves depending on a measurement site (depth) in the living body and, for example, a frequency smaller than the natural frequency of the transmission transducer 421 by 0.5 MHz is set as a natural frequency $f_B$ of the reception transducer 431. From a combination of the film thickness dimension $t_A$ of the transmitting piezoelectric film 413B that satisfies the natural frequency $f_A$ set above and the opening width $L_A$ of the first opening 411A, and a combination of the film thickness dimension $t_B$ of the receiving piezoelectric film 414A that satisfies the natural frequency $f_B$ and the opening width $L_B$ of the second opening 411B, a combination in which the figure of merit exceeds 750,000 in the transmission/reception process of the ultrasonic waves is obtained, and more preferably a combination having the largest figure of merit is obtained. The transmission transducer 421 and the reception transducer 431 are formed to have the film thickness dimension $t_A$ of the transmitting piezoelectric film 413B, the opening width $L_A$ of the first opening 411A, the film thickness dimension $t_B$ of the receiving piezoelectric film 414A, and the opening width $L_B$ of the second opening 411B which are obtained in the manner described above.

In this manner, the ultrasonic device 4 having the optimal transmission/reception efficiency with respect to a desired ultrasonic frequency is configured.

Configuration of Acoustic Lens

Back to FIG. 3, the acoustic lens 7 that configures the ultrasonic sensor 22 is described.

The acoustic lens 7 efficiently propagates, to the living body, the ultrasonic waves transmitted from the ultrasonic device 4, and efficiently propagates, to the ultrasonic device 4, the ultrasonic waves reflected from the living body. The acoustic lens 7 is disposed on a surface through which the ultrasonic device 4 transmits and receives the ultrasonic waves. Note that, although omitted from the figures, the acoustic matching layer is provided between the ultrasonic device 4 and the acoustic lens 7. The acoustic lens 7 and the acoustic matching layer is made of silicone or the like, and acoustic impedance of the ultrasonic transducers (the transmission transducer 421 and the reception transducer 431) of the element substrate 411 is set to immediate acoustic impedance between the acoustic impedance of the ultrasonic transducers and acoustic impedance of the living body.

Configuration of Circuit Board

Next, back to FIG. 2, the circuit board 6 will be described.

The circuit board 6 is provided with a plurality of drive signal terminals (not illustrated), a plurality of received signal terminals (not illustrated), and a plurality of common signal terminals (not illustrated), and the ultrasonic device 4 is connected to the circuit board with a wiring member 5. Specifically, each of the plurality of drive signal terminals is connected to the corresponding first signal terminal SA connected to the lower electrode 413A of the transmission transducer 421, and each of the plurality of received signal terminals is connected to the corresponding second signal terminal SB connected to the first electrode 414B of the reception transducer 431. Each of the plurality of common signal terminals is connected to the common terminal CA.

In addition, the circuit board 6 is provided with a driver circuit or the like for driving the ultrasonic device 4. Specifically, as illustrated in FIG. 2, the circuit board 6 is configured to have a transmission circuit 61, a reception circuit 62, a polarization voltage outputting unit 63, a transmission selecting circuit 64, a reception selecting circuit 65, or the like.

The transmission circuit 61 outputs, to the transmission selecting circuit 64, the drive voltage having a pulse waveform for driving the transmission transducer 421 through the control by the control device 10.

The reception circuit 62 outputs, to the control device 10, an output voltage (reception signal) output from the reception transducer 431. The reception circuit 62 is configured to have an amplifier circuit, a low pass filter, an A/D converter, a phase adding circuit, or the like. The reception circuit converts the received signal into a digital signal, removes a noise component, performs amplification to a predetermined signal level, and performs the signal processing for the phase adding processing for each reception channel. Then, the reception circuit outputs a reception signal after the process to the control device 10.

The polarization voltage outputting unit 63 outputs the polarization voltage for performing the polarization process of the transmitting piezoelectric film 413B and the receiving piezoelectric film 414A.

In order to maintain the transmission/reception efficiency of the transmission transducer 421 and the reception transducer 431, it is necessary to apply an electric field of 200 kV/cm or higher so as to initialize a polarizing direction for both of the transmitting piezoelectric film 413B and the receiving piezoelectric film 414A before the transmission/reception process of the ultrasonic waves is performed (or every certain cycle). In the electric field of lower than 200 kV/cm, the initialization of the polarizing direction of the piezoelectric films is insufficiently performed and the transmission/reception efficiency is reduced.

In addition, as described above, the receiving piezoelectric film 414A has a higher withstand voltage than that of the transmitting piezoelectric film 413B, and the dielectric breakdown is unlikely to occur. In addition, in the reception piezoelectric element 414, the distance between the first electrode 414B and the second electrode 414C is, for example, 5 μm, and the polarization voltage (reception polarization voltage VB) for performing appropriate polarization process increases. However, in the transmission piezoelectric element 413, the distance between the lower electrode 413A and the upper electrode 413C is the film thickness dimension $t_A$ of the transmitting piezoelectric film 413B. Therefore, the polarization voltage (transmission polarization voltage VA) for performing appropriate polarization process regardless of the occurrence of the dielectric breakdown is sufficiently smaller than that of the reception polarization voltage VB. In other words, in the embodiment, the polarization voltage outputting unit 63 applies the transmission polarization voltage VA and the reception polarization voltage VB having a relationship of VA<VB to the transmitting piezoelectric film 413B and the receiving piezoelectric film 414A.

The transmission selecting circuit 64 performs switching, based on the control by the control device 10, between ultrasonic transmitting connection of connecting the ultrasonic transmitters 42 (first signal terminal SA) and the transmission circuit 61 and transmission polarizing connection of connecting the ultrasonic transmitters 42 (first signal terminal SA) and the polarization voltage outputting unit 63.

The reception selecting circuit 65 performs switching, based on the control by the control device 10, between ultrasonic receiving connection of connecting the ultrasonic receiver 43 (second signal terminal SB) and the reception circuit 62 and reception polarizing connection of connecting the ultrasonic receiver 43 (second signal terminal SB) and the polarization voltage outputting unit 63.

Configuration of Control Device

As illustrated in FIG. 2, the control device 10 is configured to include an operating unit 11, a display unit 12, a storage unit 13, and a controller 14. For example, the control device 10 may use a terminal device such as a tablet terminal, a smartphone, or a personal computer, and may be a dedicated terminal device for operating the ultrasonic probe 2.

The operating unit 11 is a user interface (UI) through which a user operates the ultrasonic measuring device 1, and can be formed of a touch panel, an operating button, a keyboard, a mouse, or the like which are provided on the display unit 12.

The display unit 12 is configured of a liquid crystal display or the like, and displays an image.

The storage unit 13 stores various types of programs and various types of data for controlling the ultrasonic measuring device 1.

The controller 14 is configured to have an arithmetic circuit such as a central processing unit (CPU), a processing circuit that performs various types of processes which will be described below, and the storage circuit such as a memory. The controller 14 performs reading of the various types of programs stored in the storage unit 13, thereby functioning as a transmission/reception control unit 141, a signal processing unit 142, and a polarization control unit 143.

When an operation signal indicating the performing of the ultrasonic measurement is input from the operating unit 11, the transmission/reception control unit 141 causes the transmission selecting circuit 64 to perform switching to the ultrasonic transmitting connection and causes the reception selecting circuit 65 to perform switching to the ultrasonic receiving connection. The transmission/reception control unit 141 outputs the drive voltage from the transmission circuit 61 and transmits the ultrasonic waves from the transmission transducers 421. In addition, the transmission/reception control unit 141 acquires the received signal output from the reception circuit 62.

The signal processing unit 142 performs a predetermined process based on the received signal acquired from the reception circuit 62. For example, the signal processing unit 142 generates an internal tomographic image of the living body based on the received signal, and outputs the image to the display unit 12 or performs a measurement process of bloodstream or blood pressure.

For example, the polarization control unit 143 causes the transmission selecting circuit 64 to perform switching to the transmission polarizing connection at a predetermined timing and causes the reception selecting circuit 65 to perform switching to the reception polarizing connection. Examples of the timing include when a power source of the ultrasonic measuring device 1 is switched from an off state to an on state or immediately before the measurement processing is performed by the transmission/reception control unit 141, every certain period, or the like.

Operational Effect of Embodiment

The ultrasonic device 4 of the embodiment includes the transmission transducer 421 and the reception transducer 431. The transmission transducer 421 is configured to have the support film 412 (first vibration portion 412A) that covers the first opening 411A of the element substrate 411 and the transmission piezoelectric element 413 provided on the first vibration portion 412A. The transmission piezoelectric element 413 includes the transmitting piezoelectric film 413B sandwiched between the lower electrode 413A and the upper electrode 413C in the thickness direction. In addition, the reception transducer 431 is configured to have the support film 412 (second vibration portion 412B) that covers the second opening 411B of the element substrate 411 and the reception piezoelectric element 414 provided on the second vibration portion 412B. The reception piezoelectric element 414 has a configuration in which the receiving piezoelectric film 414A provided on the second vibration portion 412B is sandwiched between the first electrode 414B and the second electrode 414C in an intersecting direction (in the embodiment, the X direction orthogonal to the thickness direction) intersecting with the thickness direction. In the embodiment, the film thickness dimension $t_B$ of the receiving piezoelectric film 414A is formed to be smaller than the film thickness dimension $t_A$ of the transmitting piezoelectric film 413B.

In a case where the ultrasonic waves are transmitted by using the transmission transducer 421, and the predetermined drive voltage is applied between the electrodes, it is necessary to increase a displacement amount of the piezoelectric film, and the displacement amount is inversely proportional to the distance between the electrodes in a qualitative manner. In the embodiment, the distance between the lower electrode 413A and the upper electrode 413C is the film thickness dimension $t_A$ of the transmitting piezoelectric film 413B, and thus it is possible to sufficiently increase the transmitting sensitivity.

In addition, in a case where the ultrasonic waves are received in the reception transducer 431, it is necessary to acquire a large signal from the slight displacement of the second vibration portion 412B, and the signal value is qualitatively proportional to the distance between electrodes. In the embodiment, the distance between the electrodes of the first electrode 414B and the second electrode 414C has a value that is sufficiently larger than the film thickness dimension $t_B$ of the receiving piezoelectric film 414A, and thus it is possible to sufficiently increase the receiving sensitivity.

Accordingly, compared to a case where the transmission and the reception of the ultrasonic waves are performed by one ultrasonic transducer or a case of using the piezoelectric films having the same film thickness dimension in the transmission transducer and the reception transducer, it is possible for the transmission transducer 421 to have high transmission efficiency of the ultrasonic waves and it is possible for the reception transducer 431 to have high reception efficiency of the ultrasonic waves.

In addition to this, the contour lines of the figures of merit in FIGS. 12 to 15 have a shape in which the contour lines approach the vertical axis in parallel. In other words, when $t_B$ is small, the figure of merit is higher, compared to a case where $t_A$ is small. In this manner, a relationship of $t_B<t_A$ is satisfied, and thereby it is possible to effectively increase the figure of merit, that is, it is possible to remarkably improve the transmission/reception efficiency of the ultrasonic device 4.

In addition, in the embodiment, the film thickness dimension $t_A$ of the transmitting piezoelectric film 413B is preferably 300 nm to 1800 nm, and more preferably 500 nm to 1800 nm. In addition, the film thickness dimension $t_B$ of the receiving piezoelectric film 414A is 80 nm or larger.

In such a configuration, while the dielectric breakdown of the transmitting piezoelectric film 413B and the receiving piezoelectric film 414A is reduced, it is possible to obtain the ultrasonic device 4 having high transmission/reception efficiency.

In the embodiment, the natural frequency of the transmission transducer 421 is set to be larger by 0.2 MHz to 0.8 MHz (more preferably, 0.5 MHz) than the natural frequency $f_A$ of the transmission transducer 421 and the natural frequency $f_B$ of the reception transducer 431.

When the transmission transducer 421 and the reception transducer 431 have the equal natural frequency as each other, and the ultrasonic waves are transmitted from the transmission transducer 421, the reception transducer 431 resonates, and the output voltage containing the noise component is output and has an influence on the reception accuracy of the ultrasonic sounds. In the embodiment, since the natural frequencies of the transmission transducer 421 and the reception transducer 431 are different from each other, it is possible to reduce the noise due to such a resonance, and it is possible to improve the reception accuracy.

Here, in a case where $f_A-f_B<0.2$ MHz, it is not possible to sufficiently control the resonance of the reception transducer 431 during the transmission of the ultrasonic waves, and thus the reception accuracy is reduced. In addition, in a case where $f_A-f_B>0.8$ MHz, a difference between the frequency of the ultrasonic waves transmitted from the transmission transducer 421 and the frequency of the ultrasonic waves that is suitable to be received by the reception transducer 431 increases, and thus the reception accuracy is reduced in the reception transducer. In this respect, in the range described above, while mixture of the noise component into the output voltage, which is output from the reception transducer 431, is reduced, it is possible for the reception transducer 431 to receive reflected waves of the ultrasonic waves transmitted from the transmission transducer 421 with high receiving sensitivity, and improvement in the transmission/reception efficiency of the ultrasonic waves is achieved in the ultrasonic device 4.

In addition, in the embodiment, the natural frequency $f_B$ of the reception transducer 431 is set to be smaller than the natural frequency $f_A$ of the transmission transducer 421. In this case, since the opening width $L_B$ of the second opening 411B in the reception transducer 431 increases, the second vibration portion 412B is easily bent, and the improvement in the receiving sensitivity is achieved in the reception transducer 431.

In the embodiment, the circuit board 6 is provided with the polarization voltage outputting unit 63, and the polarization voltage outputting unit 63 applies the transmission polarization voltage VA to the transmitting piezoelectric film 413B and performs the polarization process before the transmission/reception process of the ultrasonic waves is performed in the ultrasonic device 4, and the polarization voltage outputting unit applies the reception polarization voltage VB larger than the transmission polarization voltage VA to the receiving piezoelectric film 414A and performs the polarization process. When the reception polarization voltage VB is applied to the transmitting piezoelectric film 413B, there is a concern that the dielectric breakdown will occur in the transmitting piezoelectric film 413B due to a very large voltage. When the transmission polarization voltage VA is applied to the receiving piezoelectric film 414A, it is not possible for the sufficient polarization process to be performed, and the receiving sensitivity is considered to be reduced. However, in the embodiment, it is possible to apply the optimal polarization voltage to each of the transmitting piezoelectric film 413B and the receiving piezoelectric film 414A, and it is possible to maintain high transmission/reception efficiency of the transmission transducer 421 and the reception transducer 431.

As described above, in the embodiment, since the transmission/reception efficiency is high in the ultrasonic device 4, it is possible to appropriately perform the transmission/reception process of the ultrasonic waves even in a case where the ultrasonic measurement into the living body is performed by using the ultrasonic probe 2. In addition, the control device 10 is capable of performing highly accurate measurement process (for example, generation of the internal tomographic image, measurement of bloodstream or blood pressure, or the like), based on the results from the ultrasonic measurement obtained by the corresponding ultrasonic device 4.

Modification Example

Note that, the invention is not limited to the embodiments described above, and the invention also includes a configuration obtained through modification, improvement, and an appropriate combination of the embodiments in a range in which it is possible to achieve the object of the invention.

In the embodiments described above, in order to obtain the natural frequency $f_B$ of the reception transducer 431 which is smaller than the natural frequency $f_A$ of the transmission transducer 421, an example of having a large opening width of the second opening 411B is described. However, the film thickness dimension of the receiving piezoelectric film 414A may be small, or the film thickness dimension of the receiving piezoelectric film 414A may be small while the second opening 411B has the large opening width. As described above, the receiving piezoelectric film 414A has a higher withstand voltage than that of the transmitting piezoelectric film 413B, and the dielectric breakdown is unlikely to occur. Accordingly, as described above, even in a case where the film thickness dimension of the receiving piezoelectric film 414A is small, there is no increase in a risk of occurrence of the dielectric breakdown, and thus it is possible to realize high transmission/reception efficiency.

Further, in the embodiments and modification example described above, the natural frequency $f_B$ of the reception transducer 431 is smaller than the natural frequency $f_A$ of the transmission transducer 421, and thereby the reduction in the receiving sensitivity is reduced due to the resonance; however, the invention is not limited thereto. For example, the natural frequency $f_A$ of the transmission transducer 421 may be smaller than the natural frequency $f_B$ of the reception transducer 431. In the reception transducer 431 of the embodiment, it is possible to realize the high receiving sensitivity, compared to a configuration in the related art, in which the receiving piezoelectric film is sandwiched between the two electrodes in the thickness direction. Hence, in the embodiment, the opening width of the second opening 411B is large, or the film thickness dimension of the transmitting piezoelectric film 413B is small, and thereby the transmitting sensitivity may be improved.

Further, the embodiments and modification examples employ an example in which the natural frequency $f_B$ of the reception transducer 431 or the natural frequency $f_A$ of the transmission transducer 421 are reduced to be lower than the natural frequency (for example, 8 MHz) as a target frequency; however, the natural frequencies may be designed to be higher than the natural frequency as the target.

In addition, the difference between the natural frequency $f_A$ of the transmission transducer 421 and the natural frequency $f_B$ of the reception transducer 431 is 0.2 MHz to 0.8 MHz; however, the difference is not limited thereto. For example, in a case where so-called harmonic processing of receiving a high frequency from a measurement target by the reception transducer 431 is performed or the like, the natural frequency $f_B$ of the reception transducer 431 may be set, depending on a frequency (integer multiple of $f_A$) of high frequency.

Further, an example in which the natural frequency $f_A$ of the transmission transducer 421 and the natural frequency $f_B$ of the reception transducer 431 have different values from each other is employed; however, the invention is not limited thereto, and the same natural frequency may be used.

For example, in the embodiment, the ultrasonic transmitter 42 and the ultrasonic receiver 43 are alternately disposed in the X direction; however, on the element substrate 41, the transmission region that is provided with only ultrasonic transmitters 42 may be separately provided from the reception region that is provided with only the ultrasonic receivers 43. In this case, a damping member that absorbs vibration is provided between the transmission region and the reception region. In addition, a transmission substrate, on which only the ultrasonic transmitters 42 are provided, and a reception substrate, on which only the ultrasonic receivers are provided, may be separately provided. In such a configuration, transmission of vibration from the transmission region (transmission substrate) to the reception region (reception substrate) is reduced, and it is possible to reduce noise by resonance.

The embodiment employs an example in which the first opening 411A and the second opening 411B are configured to have a rectangular shape when viewed in the thickness direction of the element substrate 411; however, the shape is not limited thereto. For example, a circular shape may be formed, or another polygonal shape may be formed.

The embodiment employs an example in which the reception transducer 431 includes the first electrode 414B and the second electrode 414C provided on the top surface (opposite side to the support film 412) of the receiving piezoelectric film 414A on the support film 412; however, the invention is not limited thereto.

Figure 17:
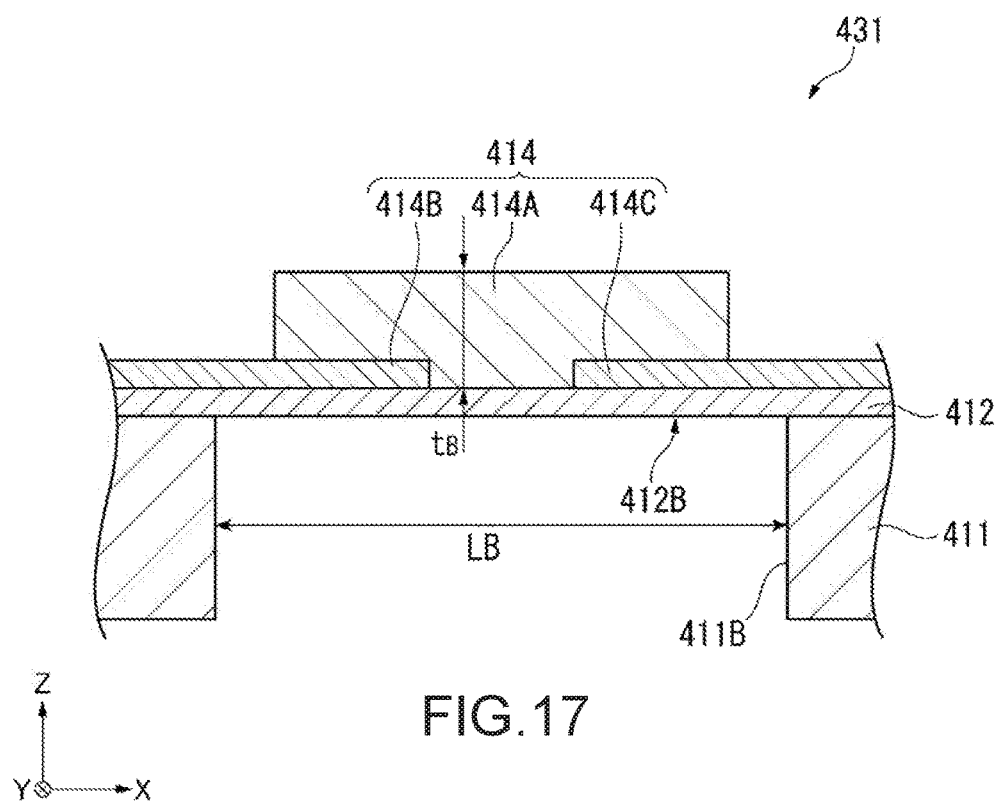
FIG. 17 is a view illustrating a modification example of the reception transducer.
Figure 18:
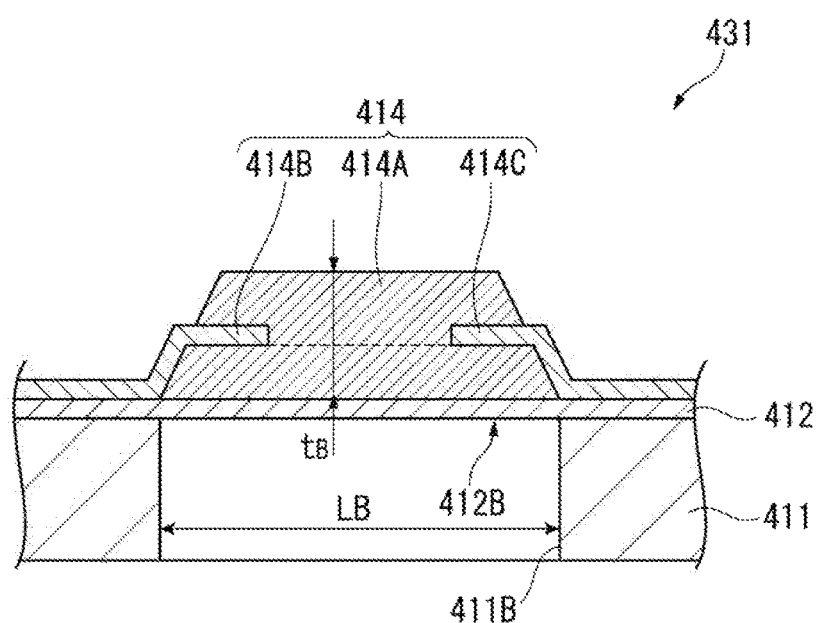
FIG. 18 is a view illustrating another modification example of the reception transducer.

FIGS. 17 and 18 are sectional views illustrating another example of the reception transducer.

As illustrated in FIG. 17, the reception transducer 431 may be configured to have the first electrode 414B and the second electrode 414C provided on the support film 412 and to have the receiving piezoelectric film 414A stacked on the first electrode 414B and the second electrode 414C. In other words, a configuration in which the first electrode 414B and the second electrode 414C are disposed between the receiving piezoelectric film 414A and the support film 412 may be employed.

In addition, as illustrated in FIG. 18, the reception transducer 431 may be configured to have the first electrode 414B and the second electrode 414C which are embedded inside the receiving piezoelectric film 414A.

In such configurations, since an air layer is not interposed between the first electrode 414B and the second electrode 414C, it is possible to effectively reduce the occurrence of the dielectric breakdown.

In addition, in the embodiments and the examples in FIGS. 17 and 18, the first electrode 414B and the second electrode 414C are disposed in the X direction orthogonal to the thickness direction (Z direction); however, the first electrode 414B and the second electrode 414C may be disposed in the Y direction, or the first electrode 414B and the second electrode 414C may be disposed in a direction inclined with respect to the X direction and the Y direction.

In addition, the direction, in which the electrodes are disposed, is not limited to a direction orthogonal to the Z direction. A distance of the first electrode 414B from the support film 412 may be different from a distance of the second electrode 414C from the support film 412. For example, a configuration, in which any one of the first electrode 414B and the second electrode 414C is provided at a boundary position between the support film 412 and the receiving piezoelectric film 414A, and the other electrode is embedded in the receiving piezoelectric film 414A, may be employed.

The embodiment described above employs an example in which the ultrasonic device 4 is provided with the reinforcing plate on the side of the support film 412 opposite to the element substrate 411, the ultrasonic waves are transmitted to the opposite side to the first opening 411A side, and the ultrasonic waves are received from an opposite side to the second opening 411B; however, the invention is not limited thereto. For example, a configuration in which the reinforcing plate is bonded to the element substrate 411 on the support film 412 side via resin may be employed. In this case, the transmission transducer 421 transmits the ultrasonic waves to the first opening 411A side and the reception transducer 431 receives the ultrasonic waves incident to the second opening 411B side.

In the embodiment described above, the ultrasonic measuring device that measures a part of the living body as a measurement target is described as an example; however, the invention is not limited thereto. For example, the invention can be applied to an ultrasonic measuring device that detects a defect of a structure, with various type of structures as the measurement target, and checks for aging. In addition, the invention can also be applied to an ultrasonic measuring device that detects a defect of a measurement target, with a semiconductor package, a wafer, or the like as the measurement target. In particular, in the invention, since the reception transducer 431 has very high receiving sensitivity, it is possible to receive the ultrasonic waves with high sensitivity even in a case where ultrasonic attenuation is large from the measurement target. Accordingly, it is possible to perform the ultrasonic measurement with high transmission/reception efficiency regardless of the measurement target by using the ultrasonic device 4 that has the opening widths of the first opening 411A and the second opening 411B and the film thickness dimensions of the transmitting piezoelectric film 413B and the receiving piezoelectric film 414A depending on the frequency of the ultrasonic waves from the measurement target. In addition, in a case where the first opening 411A or the second opening 411B are formed to be larger depending on the frequency of the ultrasonic waves from the measurement target, the film thickness dimension of the transmitting piezoelectric film may be 1800 nm or smaller.

In the embodiment described above, it is preferable that the film thickness dimension of the transmitting piezoelectric film 413B is 300 nm or larger, and the film thickness dimension of the receiving piezoelectric film 414A is 80 nm or larger; however, the invention is not limited thereto. In other words, in a case where a piezoelectric material other than PZT is used as the material of the transmitting piezoelectric film 413B or the receiving piezoelectric film 414A, it is possible to define the minimum film thickness dimension depending on the pressure resistance of the materials.

In addition, the specific structure of the embodiment of the invention may be configured by combining the embodiments and modification examples in a range in which it is possible to achieve the object of the invention, and may be appropriately modified to have another structure.

The entire disclosure of Japanese Patent Application No. 2016-163344 filed Aug. 24, 2016 is expressly incorporated by reference herein.

What is claimed is:

1. An ultrasonic device comprising:
   a substrate provided with a first opening and a second opening;
   a support film that is provided on the substrate and spans the first opening and the second opening;
   a plurality of transmission transducers connected in series, each of the plurality of transmission transducers being configured to transmit an ultrasonic wave, each of the plurality of transmission transducers being configured with a transmitting piezoelectric film and two electrodes applying a voltage to the transmitting piezoelectric film, the two electrodes sandwiching the transmitting piezoelectric film in a plan view, the transmitting piezoelectric film being provided on the support film at a position which overlaps the first opening in the plan view; and a plurality of reception transducers connected in series, each of the plurality of transmission transducers being configured to receive the ultrasonic wave, each of the plurality of reception transducers being configured with a receiving piezoelectric film and two electrodes applying a voltage to the receiving piezoelectric film, the two electrodes sandwiching the receiving piezoelectric film in a direction intersecting a direction of the plan view, the receiving piezoelectric film being provided on the support film at a position which overlaps the second opening in the plan view, wherein a film thickness dimension of the receiving piezoelectric film is smaller than a film thickness dimension of the transmitting piezoelectric film.

2. The ultrasonic device according to claim 1, wherein the film thickness dimension of the transmitting piezoelectric film is in a range of 300 nm to 1800 nm, and wherein the film thickness dimension of the receiving piezoelectric film is 80 nm or larger.

3. The ultrasonic device according to claim 1, wherein the support film is configured with a first vibration portion that spans the first opening and a second vibration portion that spans the second opening, and wherein a first natural frequency of each of the plurality of transmission transducers is different from a second natural frequency of each of the plurality of reception transducers.

4. The ultrasonic device according to claim 3, wherein a difference between the first natural frequency and the second natural frequency is in a range of 0.2 MHz to 0.8 MHz.

5. The ultrasonic device according to claim 3, wherein the second natural frequency is lower than the first natural frequency.

6. An ultrasonic module comprising:

an ultrasonic device, the ultrasonic device including:
  a substrate provided with a first opening and a second opening;
  a support film that is provided on the substrate and spans the first opening and the second opening;
  a plurality of transmission transducers connected in series, each of the plurality of transmission transducers being configured to transmit an ultrasonic wave, each of the plurality of transmission transducers being configured with a transmitting piezoelectric film and two electrodes applying a voltage to the transmitting piezoelectric film, the two electrodes sandwiching the transmitting piezoelectric film in a plan view, the transmitting piezoelectric film being provided on the support film at a position which overlaps the first opening in the plan view; and
  a plurality of reception transducers connected in series, each of the plurality of transmission transducers being configured to receive the ultrasonic wave, each of the plurality of reception transducers being configured with a receiving piezoelectric film and two electrodes applying a voltage to the receiving piezoelectric film, the two electrodes sandwiching the receiving piezoelectric film in a direction intersecting a direction of the plan view, the receiving piezoelectric film being provided on the support film at a position which overlaps the second opening in the plan view; and a housing that accommodates the ultrasonic device, wherein a film thickness dimension of the receiving piezoelectric film is smaller than a film thickness dimension of the transmitting piezoelectric film.

7. An ultrasonic measuring device comprising:

an ultrasonic device, the ultrasonic device including:
  a substrate provided with a first opening and a second opening;
  a plurality of transmission transducers connected in series, each of the plurality of transmission transducers being configured to transmit an ultrasonic wave, each of the plurality of transmission transducers being configured with a transmitting piezoelectric film and two electrodes applying a voltage to the transmitting piezoelectric film, the two electrodes sandwiching the transmitting piezoelectric film in a plan view, the transmitting piezoelectric film being provided on the support film at a position which overlaps the first opening in the plan view; and
  a plurality of reception transducers connected in series, each of the plurality of transmission transducers being configured to receive the ultrasonic wave, each of the plurality of reception transducers being configured with a receiving piezoelectric film and two electrodes applying a voltage to the receiving piezoelectric film, the two electrodes sandwiching the receiving piezoelectric film in a direction intersecting a direction of the plan view, the receiving piezoelectric film being provided on the support film at a position which overlaps the second opening in the plan view; and a controller that controls the ultrasonic device, wherein a film thickness dimension of the receiving piezoelectric film is smaller than a film thickness dimension of the transmitting piezoelectric film.

* * * * *